United States Patent
Bourque et al.

(10) Patent No.: US 9,861,355 B2
(45) Date of Patent: *Jan. 9, 2018

(54) SUTURE PASSING

(71) Applicant: Smith & Nephew, Inc., Memphis, TN (US)

(72) Inventors: Bernard J. Bourque, Taunton, MA (US); Michael C. Ferragamo, Foster, RI (US)

(73) Assignee: Smith & Nephew, Inc., Memphis, TN (US)

( * ) Notice: Subject to any disclaimer, the term of this patent is extended or adjusted under 35 U.S.C. 154(b) by 217 days.

This patent is subject to a terminal disclaimer.

(21) Appl. No.: 14/666,031

(22) Filed: Mar. 23, 2015

(65) Prior Publication Data

US 2015/0366558 A1    Dec. 24, 2015

Related U.S. Application Data

(63) Continuation of application No. 11/153,908, filed on Jun. 16, 2005, now Pat. No. 8,986,343.
(Continued)

(51) Int. Cl.
*A61B 17/04* (2006.01)
*A61B 17/00* (2006.01)
(Continued)

(52) U.S. Cl.
CPC .............. *A61B 17/0469* (2013.01); *A61B 2017/00349* (2013.01); *A61B 2017/00477* (2013.01);
(Continued)

(58) Field of Classification Search
CPC ............ A61B 17/0469; A61B 17/2816; A61B 2017/00349; A61B 2017/2837
See application file for complete search history.

(56) References Cited

U.S. PATENT DOCUMENTS 349,791 A    9/1886  Gibboney, Jr.
373,372 A   11/1887  King
(Continued)

FOREIGN PATENT DOCUMENTS

CN    201930033 U    8/2011
DE       245573 C    4/1912
(Continued)

OTHER PUBLICATIONS

International Search Report for PCT/US2005/021289 dated Nov. 21, 2005.
(Continued)

*Primary Examiner* — Katherine Rodjom
(74) *Attorney, Agent, or Firm* — Burns & Levinson LLP; Joseph M. Maraia

(57) ABSTRACT

A surgical device includes a first member, deformable to move a pair of opposing projections toward one another. The projections are received in a pair of opposing openings in a second member, so the first member can pivot relative to the second member about an axis defined by the projections. In another aspect, a surgical instrument includes a first pinless joint pivotably coupling a first jaw to a second jaw, a second pinless joint coupling a distal end of an actuating member to the first jaw, and a third pinless joint coupling a handle to a proximal end of the actuating member. The third pinless joint translates movement of the handle into axial movement of the actuating member, and the second pinless joint translates axial movement of the actuating member into pivotable movement of the first jaw relative to the second jaw about the first pinless joint.

6 Claims, 25 Drawing Sheets

Related U.S. Application Data

(60) Provisional application No. 60/579,682, filed on Jun. 16, 2004.

(51) Int. Cl.
  *A61B 17/06* (2006.01)
  *A61B 17/28* (2006.01)

(52) U.S. Cl.
  CPC ............ *A61B 2017/06019* (2013.01); *A61B 2017/06042* (2013.01); *A61B 2017/06095* (2013.01); *A61B 2017/2837* (2013.01)

(56) References Cited

U.S. PATENT DOCUMENTS

| | | |
|---|---|---|
| 421,919 A | 2/1890 | Fergen |
| 424,518 A | 4/1890 | Van Norman |
| 652,175 A | 6/1900 | Felson |
| 659,422 A | 10/1900 | Shidler |
| 671,337 A | 4/1901 | Gibson |
| 919,138 A | 4/1909 | Drake et al. |
| 1,009,065 A | 11/1911 | Hahn et al. |
| 1,037,864 A | 9/1912 | Carlson et al. |
| 1,293,565 A | 2/1919 | Smit |
| 1,579,379 A | 4/1926 | Marbel |
| 1,635,066 A | 7/1927 | Wells |
| 1,641,077 A | 8/1927 | Fouguet |
| 1,656,467 A | 1/1928 | Blake |
| 1,815,725 A | 7/1931 | Pilling et al. |
| 1,822,330 A | 9/1931 | Ainslie |
| 1,855,546 A | 4/1932 | File |
| 1,856,721 A | 5/1932 | Nagelmann |
| 1,876,792 A | 9/1932 | Thompson |
| 1,933,024 A | 10/1933 | Nagelmann |
| 2,042,403 A | 5/1936 | Hrivnak |
| 2,065,659 A | 12/1936 | Cullen |
| 2,212,830 A | 9/1940 | Anastasi |
| 2,316,297 A | 4/1943 | Southerland et al. |
| 2,348,218 A | 5/1944 | Karle |
| 2,411,118 A | 11/1946 | Schuster |
| 2,414,882 A | 1/1947 | Longfellow |
| 2,434,133 A | 1/1948 | Volk |
| 2,577,240 A | 12/1951 | Findley |
| 2,579,192 A | 12/1951 | Kohl |
| 2,593,622 A | 4/1952 | Stanelle |
| 2,601,564 A | 6/1952 | Smith |
| 2,610,631 A | 9/1952 | Calicchio |
| 2,646,045 A | 7/1953 | Priestley |
| 2,808,055 A | 10/1957 | Thayer |
| 2,880,728 A | 4/1959 | Rights |
| 2,895,478 A | 7/1959 | Post |
| 2,959,172 A | 11/1960 | Held |
| 3,013,559 A | 12/1961 | Thomas |
| 3,036,482 A | 5/1962 | Kenworthy et al. |
| 3,073,311 A | 1/1963 | Tibbs et al. |
| 3,139,089 A | 6/1964 | Schwerin |
| 2,738,790 A | 3/1965 | Todt et al. |
| 3,349,772 A | 10/1967 | Rygg |
| 3,417,752 A | 12/1968 | Butler |
| 3,470,834 A | 10/1969 | Bone |
| 3,470,875 A | 10/1969 | Johnson |
| 3,638,653 A | 2/1972 | Berry |
| 3,687,138 A | 8/1972 | Jarvik |
| 3,716,058 A | 2/1973 | Tanner, Jr. |
| 3,752,516 A | 8/1973 | Mumma |
| 3,763,860 A | 10/1973 | Clarke |
| 3,840,017 A | 10/1974 | Violante |
| 3,842,824 A | 10/1974 | Neufeld |
| 3,842,840 A | 10/1974 | Schweizer |
| 3,856,018 A | 12/1974 | Perisse et al. |
| 3,871,379 A | 3/1975 | Clarke |
| 3,890,975 A | 6/1975 | McGregor |
| 3,901,244 A | 8/1975 | Schweizer |
| 3,946,740 A | 3/1976 | Bassett |
| 3,980,177 A | 9/1976 | McGregor |
| 3,985,138 A | 10/1976 | Jarvik |
| 3,990,619 A | 11/1976 | Russell |
| 4,027,608 A | 6/1977 | Arbuckle |
| 4,109,658 A | 8/1978 | Hughes |
| 4,161,951 A | 7/1979 | Scanlan, Jr. |
| 4,164,225 A | 8/1979 | Johnson et al. |
| 4,224,947 A | 9/1980 | Fukuda |
| 4,235,238 A | 11/1980 | Ogiu et al. |
| 4,236,470 A | 12/1980 | Stenson |
| 4,312,337 A | 1/1982 | Donohue |
| 4,326,531 A | 4/1982 | Shimonaka |
| 4,345,600 A | 8/1982 | Rothfuss |
| 4,373,530 A | 2/1983 | Kilejian |
| 4,384,406 A | 5/1983 | Tischlinger |
| 4,414,466 A | 11/1983 | Fischer et al. |
| 4,414,908 A | 11/1983 | Yasukata |
| 4,423,729 A | 1/1984 | Gray |
| 4,440,171 A | 4/1984 | Nomoto et al. |
| 4,441,497 A | 4/1984 | Paulder |
| 4,448,194 A | 5/1984 | DiGiovanni et al. |
| 4,463,753 A | 8/1984 | Gustilo |
| 4,471,781 A | 9/1984 | Di Giovanni et al. |
| 4,493,323 A | 1/1985 | Albright et al. |
| 4,500,024 A | 2/1985 | DiGiovanni et al. |
| 4,509,516 A | 4/1985 | Richmond |
| 4,512,344 A | 4/1985 | Barber |
| 4,535,768 A | 8/1985 | Hourahane et al. |
| 4,539,474 A | 9/1985 | Takahata |
| 4,553,544 A | 11/1985 | Nomoto et al. |
| 4,557,265 A | 12/1985 | Andersson |
| 4,574,805 A | 3/1986 | Lerner |
| 4,580,563 A | 4/1986 | Gross |
| 4,590,929 A | 5/1986 | Klien |
| 4,596,249 A | 6/1986 | Freda et al. |
| 4,602,635 A | 7/1986 | Mulhollan et al. |
| 4,662,068 A | 5/1987 | Polonsky |
| 4,712,545 A * | 12/1987 | Honkanen .......... A61B 17/1608 600/564 |
| 4,716,893 A | 1/1988 | Fischer et al. |
| 4,723,546 A | 2/1988 | Zagorski |
| 4,724,840 A | 2/1988 | McVay et al. |
| 4,739,751 A | 4/1988 | Sapega et al. |
| 4,741,330 A | 5/1988 | Hayhurst |
| 4,778,468 A | 10/1988 | Hunt et al. |
| 4,779,616 A | 10/1988 | Johnson |
| 4,781,190 A | 11/1988 | Lee |
| 4,787,377 A | 11/1988 | Laboureau |
| 4,790,312 A | 12/1988 | Capuano et al. |
| 4,836,205 A | 6/1989 | Barrett |
| 4,846,799 A | 7/1989 | Tanaka et al. |
| 4,870,957 A | 10/1989 | Globe et al. |
| 4,871,289 A | 10/1989 | Choinere |
| 4,881,537 A | 11/1989 | Henning |
| 4,884,572 A | 12/1989 | Bays et al. |
| 4,890,615 A | 1/1990 | Caspari et al. |
| 4,895,148 A | 1/1990 | Bays et al. |
| 4,899,743 A | 2/1990 | Nicholson et al. |
| 4,923,461 A | 5/1990 | Caspari et al. |
| 4,935,027 A | 6/1990 | Yoon |
| 4,950,285 A | 8/1990 | Wilk |
| 4,955,897 A | 9/1990 | Ship |
| 4,957,498 A | 9/1990 | Caspari et al. |
| 4,961,741 A | 10/1990 | Hayhurst |
| 4,976,715 A | 12/1990 | Bays et al. |
| 5,015,250 A | 5/1991 | Foster |
| 5,026,350 A | 6/1991 | Tanaka et al. |
| 5,037,422 A | 8/1991 | Hayhurst et al. |
| 5,037,433 A | 8/1991 | Wilk et al. |
| 5,053,047 A | 10/1991 | Yoon |
| 5,084,058 A | 1/1992 | Li |
| 5,085,661 A | 2/1992 | Moss |
| 5,087,263 A | 2/1992 | Li |
| 5,100,415 A | 3/1992 | Hayhurst |
| 5,100,418 A | 3/1992 | Yoon et al. |
| 5,100,421 A | 3/1992 | Christoudias |
| 5,120,318 A | 6/1992 | Nallapareddy |
| 5,123,913 A | 6/1992 | Wilk et al. |
| 5,129,912 A | 7/1992 | Noda et al. |
| 5,133,723 A | 7/1992 | Li et al. |

(56) References Cited

U.S. PATENT DOCUMENTS

| | | |
|---|---|---|
| 5,149,329 A | 9/1992 | Richardson |
| 5,152,764 A | 10/1992 | Goble |
| 5,152,769 A | 10/1992 | Baber |
| 5,152,790 A | 10/1992 | Rosenberg et al. |
| 5,163,946 A | 11/1992 | Li |
| 5,174,087 A | 12/1992 | Bruno |
| 5,176,691 A | 1/1993 | Pierce |
| 5,178,629 A | 1/1993 | Kammerer |
| 5,181,919 A | 1/1993 | Bergman et al. |
| 5,188,636 A | 2/1993 | Fedotov |
| 5,192,287 A | 3/1993 | Fournier et al. |
| 5,201,743 A | 4/1993 | Haber et al. |
| 5,201,744 A | 4/1993 | Jones |
| 5,211,650 A | 5/1993 | Noda |
| 5,217,471 A | 6/1993 | Burkhart |
| 5,217,486 A | 6/1993 | Rice et al. |
| 5,222,508 A | 6/1993 | Contarini |
| 5,222,962 A | 6/1993 | Burkhart |
| 5,222,976 A | 6/1993 | Yoon et al. |
| 5,224,955 A | 7/1993 | West |
| 5,234,443 A | 8/1993 | Phan et al. |
| 5,234,444 A | 8/1993 | Christoudias |
| 5,242,458 A | 9/1993 | Bendel et al. |
| 5,248,231 A | 9/1993 | Denham et al. |
| 5,250,054 A | 10/1993 | Li |
| 5,250,055 A | 10/1993 | Moore et al. |
| 5,254,126 A | 10/1993 | Filipi et al. |
| 5,257,637 A | 11/1993 | El Gazayerli |
| 5,259,846 A | 11/1993 | Granger et al. |
| 5,261,917 A | 11/1993 | Hasson et al. |
| 5,266,075 A | 11/1993 | Clark et al. |
| 5,269,783 A | 12/1993 | Sander |
| 5,269,786 A | 12/1993 | Morgan |
| 5,269,791 A | 12/1993 | Mayzels et al. |
| 5,273,024 A | 12/1993 | Menon et al. |
| 5,275,613 A | 1/1994 | Haber et al. |
| 5,281,234 A | 1/1994 | Wilk et al. |
| 5,282,809 A | 2/1994 | Kammerer et al. |
| 5,292,327 A | 3/1994 | Dodd et al. |
| 5,304,184 A | 4/1994 | Hathaway et al. |
| 5,304,185 A | 4/1994 | Taylor |
| 5,306,280 A | 4/1994 | Bregan et al. |
| 5,308,353 A | 5/1994 | Feurrier |
| 5,312,422 A | 5/1994 | Troll |
| 5,368,601 A | 5/1994 | Beurrier |
| 5,318,577 A | 6/1994 | Li |
| 5,320,632 A | 6/1994 | Heidmueller |
| 5,327,896 A | 7/1994 | Schmieding |
| 5,334,198 A | 8/1994 | Hart et al. |
| 5,356,419 A | 10/1994 | Chow |
| 5,364,408 A | 11/1994 | Gordon |
| 5,368,606 A | 11/1994 | Marlow et al. |
| 5,372,604 A | 12/1994 | Troll |
| 5,374,275 A | 12/1994 | Bradley |
| 5,376,096 A | 12/1994 | Foster |
| 5,382,257 A | 1/1995 | Lewis et al. |
| 5,389,103 A | 2/1995 | Melzer et al. |
| 5,391,170 A | 2/1995 | McGuire et al. |
| 5,391,173 A | 2/1995 | Wilk |
| 5,393,302 A | 2/1995 | Clark et al. |
| 5,397,325 A | 3/1995 | Della Badia et al. |
| 5,403,328 A | 4/1995 | Shallman |
| 5,403,329 A | 4/1995 | Hinchcliffe |
| 5,409,494 A | 4/1995 | Morgan |
| 5,417,699 A | 5/1995 | Klein et al. |
| 5,417,701 A | 5/1995 | Holmes |
| 5,423,837 A | 6/1995 | Mericle et al. |
| 5,425,733 A | 6/1995 | Schmieding |
| 5,433,722 A | 7/1995 | Shame et al. |
| 5,441,502 A | 8/1995 | Barlett |
| 5,441,507 A | 8/1995 | Wilk |
| 5,449,367 A | 9/1995 | Kadry |
| 5,454,823 A | 10/1995 | Richardson et al. |
| 5,456,246 A | 10/1995 | Schmieding et al. |
| 5,462,562 A | 10/1995 | Elkus |
| 5,464,425 A | 11/1995 | Skiba |
| 5,466,243 A | 11/1995 | Schmieding et al. |
| 5,474,565 A | 12/1995 | Troll |
| 5,480,406 A | 1/1996 | Nolan et al. |
| 5,496,331 A | 3/1996 | Xu et al. |
| 5,496,335 A | 3/1996 | Thomason et al. |
| 5,499,991 A | 3/1996 | Garman et al. |
| 5,501,688 A | 3/1996 | Whiteside et al. |
| 5,501,692 A | 3/1996 | Riza |
| 5,505,735 A | 4/1996 | Li |
| 5,507,757 A | 4/1996 | Sauer et al. |
| 5,520,696 A | 5/1996 | Wenstrom, Jr. |
| 5,520,703 A | 5/1996 | Essig et al. |
| 5,522,820 A | 6/1996 | Caspari et al. |
| 5,569,301 A | 10/1996 | Granger et al. |
| 5,573,543 A | 11/1996 | Stevens |
| 5,591,180 A | 1/1997 | Hinchliffe |
| 5,603,718 A | 2/1997 | Xu |
| 5,618,290 A | 4/1997 | Toy et al. |
| 5,626,588 A | 5/1997 | Sauer et al. |
| 5,630,825 A | 5/1997 | de la Torre et al. |
| 5,674,229 A | 10/1997 | Tovey et al. |
| 5,674,230 A | 10/1997 | Tovey et al. |
| 5,690,653 A | 11/1997 | Richardson et al. |
| 5,695,522 A | 12/1997 | LeMaire, III et al. |
| 5,707,379 A | 1/1998 | Fleenor et al. |
| 5,709,694 A | 1/1998 | Greenberg et al. |
| 5,728,112 A | 3/1998 | Yoon |
| 5,741,278 A | 4/1998 | Stevens |
| 5,746,751 A | 5/1998 | Sherts |
| 5,755,728 A | 5/1998 | Maki |
| 5,759,188 A | 6/1998 | Yoon |
| 5,792,152 A | 8/1998 | Klein et al. |
| 5,810,852 A | 9/1998 | Greenberg et al. |
| 5,814,069 A | 9/1998 | Schulze et al. |
| 5,817,107 A | 10/1998 | Schaller |
| 5,827,299 A | 10/1998 | Thomason et al. |
| 5,830,220 A | 11/1998 | Wan et al. |
| 5,843,099 A | 12/1998 | Nichols et al. |
| 5,843,100 A | 12/1998 | Meade |
| 5,860,992 A | 1/1999 | Daniel et al. |
| 5,871,488 A | 2/1999 | Tovey et al. |
| 5,871,490 A | 2/1999 | Schulze et al. |
| 5,876,412 A | 3/1999 | Piraka |
| 5,899,911 A | 5/1999 | Carter |
| 5,910,148 A | 6/1999 | Reimels et al. |
| 5,919,199 A | 7/1999 | Mers Kelly et al. |
| 5,925,064 A | 7/1999 | Meyers et al. |
| 5,931,844 A | 8/1999 | Thompson et al. |
| 5,938,668 A | 8/1999 | Scirica et al. |
| 5,951,587 A | 9/1999 | Qureshi et al. |
| 5,954,733 A | 9/1999 | Yoon |
| 5,957,937 A | 9/1999 | Yoon |
| 5,980,538 A | 11/1999 | Fuchs et al. |
| 5,984,932 A | 11/1999 | Yoon |
| 5,993,467 A | 11/1999 | Yoon |
| 6,004,332 A | 12/1999 | Yoon et al. |
| 6,017,358 A | 1/2000 | Yoon et al. |
| 6,024,747 A | 2/2000 | Kontos |
| 6,077,276 A | 6/2000 | Kontos |
| 6,080,180 A | 6/2000 | Yoon et al. |
| 6,086,601 A | 7/2000 | Yoon |
| 6,117,114 A | 9/2000 | Nobles et al. |
| 6,117,144 A | 9/2000 | Nobles |
| 6,126,665 A | 10/2000 | Yoon |
| 6,143,004 A | 11/2000 | Davis et al. |
| 6,143,005 A | 11/2000 | Yoon et al. |
| 6,159,224 A | 12/2000 | Yoon |
| 6,183,485 B1 | 2/2001 | Thomason et al. |
| 6,197,035 B1 | 3/2001 | Loubens et al. |
| 6,200,329 B1 | 3/2001 | Fung et al. |
| 6,322,570 B1 | 11/2001 | Matsutani et al. |
| 6,332,889 B1 | 12/2001 | Sancoff et al. |
| 6,475,135 B1 | 11/2002 | Levy |
| 6,511,487 B1 | 1/2003 | Oren et al. |
| 6,517,552 B1 | 2/2003 | Nord et al. |
| 6,533,795 B1 | 3/2003 | Tran et al. |
| 6,551,330 B1 | 4/2003 | Bain et al. |
| 6,599,298 B1 | 7/2003 | Forster et al. |

(56) References Cited

U.S. PATENT DOCUMENTS

| | | |
|---|---|---|
| 6,599,309 B1 | 7/2003 | Gilman |
| 6,616,674 B2 | 9/2003 | Schmieding |
| 6,623,492 B1 | 9/2003 | Berube et al. |
| 6,638,283 B2 | 10/2003 | Thal |
| 6,679,895 B1 | 1/2004 | Sancoff et al. |
| 6,723,107 B1 | 4/2004 | Skiba et al. |
| 6,770,084 B1 | 8/2004 | Bain et al. |
| 2002/0065526 A1 | 5/2002 | Oren et al. |
| 2002/0103494 A1 | 8/2002 | Pacey |
| 2002/0126845 A1 | 9/2002 | Hue et al. |
| 2002/0128666 A1 | 9/2002 | Sancoff et al. |
| 2002/0138084 A1 | 9/2002 | Weber |
| 2002/0147456 A1 | 10/2002 | Diduch et al. |
| 2002/0173800 A1 | 11/2002 | Dreyfuss et al. |
| 2003/0009186 A1 | 1/2003 | Mastri et al. |
| 2003/0023250 A1 | 1/2003 | Watschke et al. |
| 2003/0065337 A1 | 4/2003 | Topper et al. |
| 2003/0078599 A1 | 4/2003 | O'Quinn et al. |
| 2003/0078600 A1 | 4/2003 | O'Quinn et al. |
| 2003/0105474 A1 | 6/2003 | Bonutti |
| 2003/0144674 A1 | 7/2003 | Loubens et al. |
| 2003/0176874 A1 | 9/2003 | Sauer |
| 2003/0216756 A1 | 11/2003 | Klein et al. |
| 2003/0233106 A1 | 12/2003 | Dreyfuss |
| 2003/0233108 A1 | 12/2003 | Gellman et al. |
| 2004/0073254 A1 | 4/2004 | Wyman et al. |
| 2004/0193185 A1 | 9/2004 | McBrayer |
| 2004/0249394 A1* | 12/2004 | Morris ............... A61B 17/0469 606/144 |
| 2004/0260314 A1 | 12/2004 | Lizardi et al. |
| 2005/0043748 A1 | 2/2005 | Oren et al. |

FOREIGN PATENT DOCUMENTS

| | | |
|---|---|---|
| DE | 321755 C | 6/1920 |
| DE | 9109097 U1 | 9/1991 |
| DE | 9112301 U1 | 11/1991 |
| DE | 9203041 U1 | 5/1992 |
| DE | 4235602 A1 | 4/1994 |
| EP | 0136262 A2 | 4/1985 |
| EP | 0207545 A1 | 1/1987 |
| EP | 0315371 A2 | 5/1989 |
| EP | 0903109 A1 | 3/1990 |
| EP | 0535906 A2 | 4/1993 |
| EP | 0574707 A1 | 12/1993 |
| EP | 0684012 A2 | 11/1995 |
| EP | 0778004 A1 | 6/1997 |
| EP | 0792621 A1 | 9/1997 |
| EP | 1243221 A2 | 9/2002 |
| EP | 1334697 A1 | 8/2003 |
| EP | 2353516 A1 | 8/2011 |
| GB | 630693 A | 10/1949 |
| GB | 2260704 A | 4/1993 |
| JP | H0542161 A | 2/1993 |
| JP | 2007050200 A | 3/2007 |
| SU | 552077 A1 | 3/1977 |
| WO | 1989010096 A1 | 11/1989 |
| WO | 1992012674 A1 | 8/1992 |
| WO | 1994028801 A1 | 12/1994 |
| WO | 1995002363 A1 | 1/1995 |
| WO | 1995008958 A1 | 4/1995 |
| WO | 1995013021 A1 | 5/1995 |
| WO | 1996009796 A2 | 4/1996 |
| WO | 1996027331 A1 | 9/1996 |
| WO | 1996039946 A1 | 12/1996 |
| WO | 1996039948 A1 | 12/1996 |
| WO | 1997041780 A1 | 11/1997 |
| WO | 1997047246 A1 | 12/1997 |
| WO | 1998014126 A1 | 4/1998 |
| WO | 1998030151 A1 | 7/1998 |
| WO | 1998030152 A1 | 7/1998 |
| WO | 1998030153 A1 | 7/1998 |
| WO | 1998043545 A1 | 10/1998 |
| WO | 1999012480 A1 | 3/1999 |
| WO | 1999047050 A2 | 9/1999 |
| WO | 2000012013 A1 | 3/2000 |
| WO | 2000051498 A1 | 9/2000 |
| WO | 2001078609 A2 | 10/2001 |
| WO | 2001095809 A1 | 12/2001 |
| WO | 2002004322 A2 | 1/2002 |
| WO | 2002043558 A2 | 6/2002 |
| WO | 2003099136 A1 | 12/2003 |
| WO | 2009138103 A1 | 11/2009 |
| WO | 2011008607 A1 | 1/2011 |
| WO | 2013119592 A1 | 8/2013 |

OTHER PUBLICATIONS

Written Opinion for PCT/US2005/021289 dated Dec. 16, 2006.
Notice of Reasons for Rejections for Japanese Patent Application No. 2012-001385, dated May 28, 2013.
Examiner's First Report on Australian Application No. 2005262460 dated Mar. 5, 2010.
Gardner, R.C. (1975), The Hand, "A Malleable Needle for Tendon Surgery," pp. 185-186.
Lore, J.M., Tender Grip Forceps, American Journal of Surgery, vol. 104, Jul. 1962.
1997 Products Catalog, Smith & Nephew Inc., Shoulder Arthroscopy, 3 pages, Printed Mar. 1997.
1998 Products Catalog, Endoscopy Division, Smith & Nephew, Inc., Shoulder Arthroscopy, 6 pages, Mar. 1998.
1999 Products Catalog, Endoscopy Division, Smith & Nephew, Inc., Shoulder Arthroscopy, 3 pages, Mar. 1999.
2001 Products Catalog U.S. Market, Endoscopy Division, Smith & Nephew, Inc., Shoulder Arthroscopy, 3 pages, Dec. 2000.
2002 Products Catalog U.S. Market, Endoscopy Division, Smith & Nephew, Inc., Knee Arthroscopy, 6 pages, Printed Dec. 2001.
Elite and Arthro-Pierce Shoulder Instrument Systems Brochure, 2001, Smith & Nephew, Inc., 4 page, printed Feb. 2001.
Introducting the Acufex Suture Punch Suturing made simple. 1997, Smith & Nephew, Inc., 1 page.
Esch, J., Arthroscopic Rotator Cuff Repair with the Elite Shoulder System, A Smith & Nephew Technique Plus Illustrated Guide, 2001, Smith & Nephew, Inc., 15 page, Oct. 2001.
Closing the Gap in Soft Tissue Repair, The AutoCuff System, 2003, Opus Medical, Inc., 4 pages.
The Elite Shoulder System Brochure, 1999, OBL, Inc., 4 pages.
Golano, P. et al., Arthroscopic Anatomy of Posterior Ankle Ligaments, Arthroscopy: The Journal of Arthroscopic and Related Surgery, vol. 18, No. 4 (Apr.), 2002: pp. 353-358.
The Easy-to-us ArthroSew Suturing System for passing braided suture fast and effectively, 1997, Surgical Dynamics, 2 pages, May 1997.
Acufex Suture Punch Suturing made simple. 1997, Smith & Nephew, Inc., 2 pages, Feb. 1997.
Field, L.D., The Elite Arthroscopic Rotator Cuff Repair Shoulder System, 1999, OBL, Inc., 4 pages.
Arthrex Transtibial PCL Reconstruction Surgical Technique Manual, 29 pages.
Arthrex, FASTak and Corkscrew Suture Anchor System for Rotator Cuff Repair, 1996 Smith & Nephew, Inc., 1 page.
Elite and Arhtro-Pierce Shoulder Instrument Systems Ordering Information, 2002, Smith & Nephew, Inc., 2 pages, Aug. 2002.
Esch, J., The Elite Arthroscopic Rotator Cuff Repair Shoulder System, 1999, OBL, Inc., 12 pages.
OBL Arthro-Pierce Making It Simple, 2000, OBL, Inc., 2 pages.
Field, L.D., The Elite Shoulder System, 1999, OBL, Inc., 4 pages.
OBL, Hospital Price List, Jul. 1, 2000, OBL, Inc., 4 pages.
From our skilled hands to yours. Hand-Held Instrument Guide, 1997, Smith & Nephew, Inc., 13 pages, Aug. 18, 1997.
The Complete System for Shoulder Arthroscopy, Innovative Solutions for Arthroscopists, 2000, T.A.G. Medical Products, 7 pages, Jan. 2001 and Feb. 2000.
Arthrex Transtibial Arthroscopic PCL Reconstruction Surgical Technique Manual, 1999, Arthrex, Inc., 27 pages.
Arthrex Transtibial Single Incision ACL Reconstruction using Three Autograft Options, 1998, Arthrex, Inc., 32 pages.

(56) References Cited

OTHER PUBLICATIONS

Suture Punch, 1993, ArthroTek, Inc., 2 pages.
The ExpressSew, Suture Passer, The 5mm Solution for Tissue Repair, 2002, Surgical Solutions, LLC, 5 pages.
Introducing the Acufex Suture Punch, 1997, Smith & Nephew, Inc., 4 pages, Jan. 1997.
ExpressSew, Suture Passer, Surgical Solutions, 5 pages, Apr. 2003.
Romeo, A. A., Arthroscopic Repair of Full-Thickness Rotator Cuff Tears: Surgical Technique and Instrumentation, Orthopedic Special Edition, vol. 7, No. 1 of 2, 2001, pp. 25-28.
Morgan, C.D. et al. "Arthoroscopic Meniscus Repair: A Safe Approach to the Posterior Horns", Arthroscopy: The Journal of Arthroscopic of Related Surgery, vol. 2, No. 1, 1986 (10 pages).

\* cited by examiner

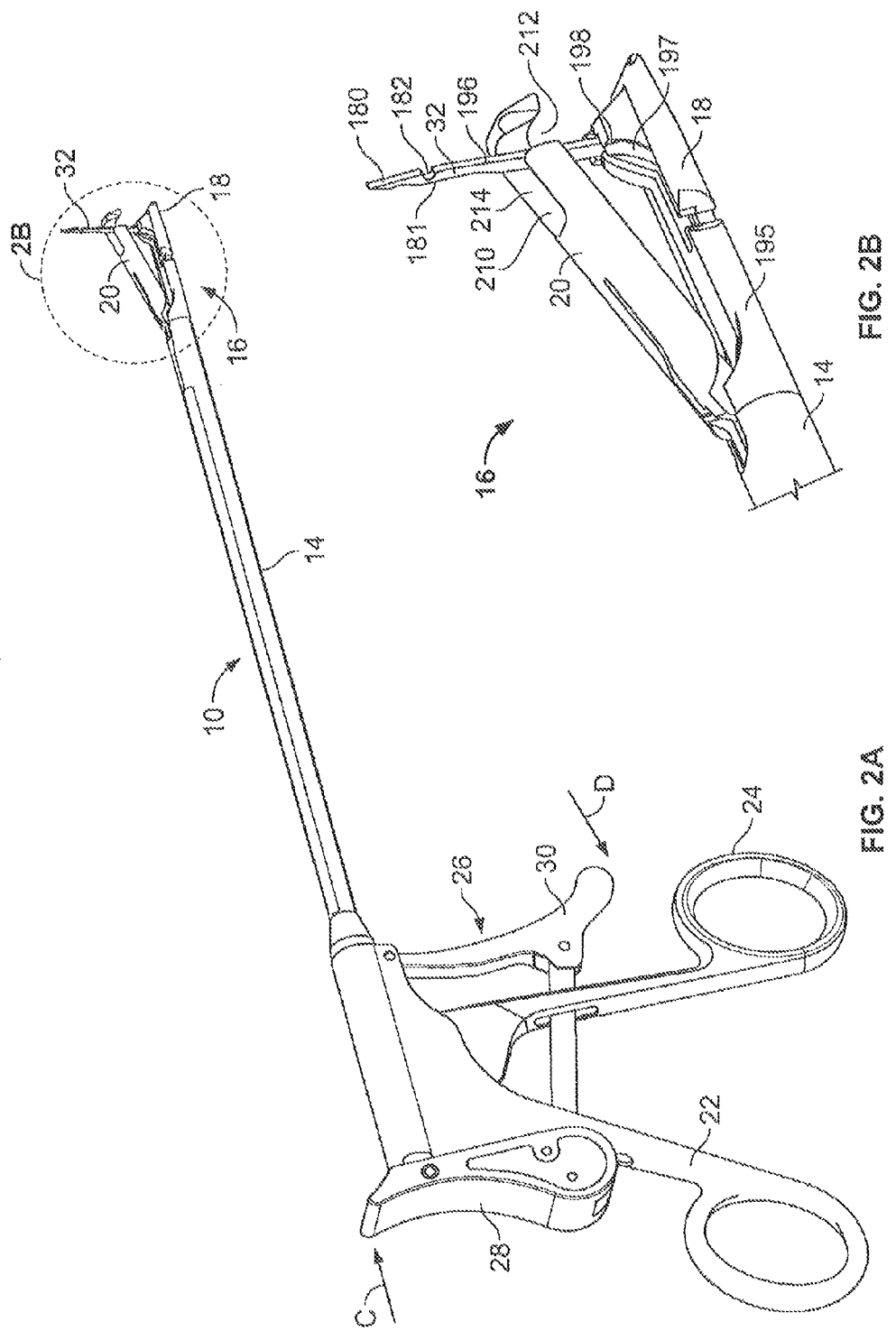

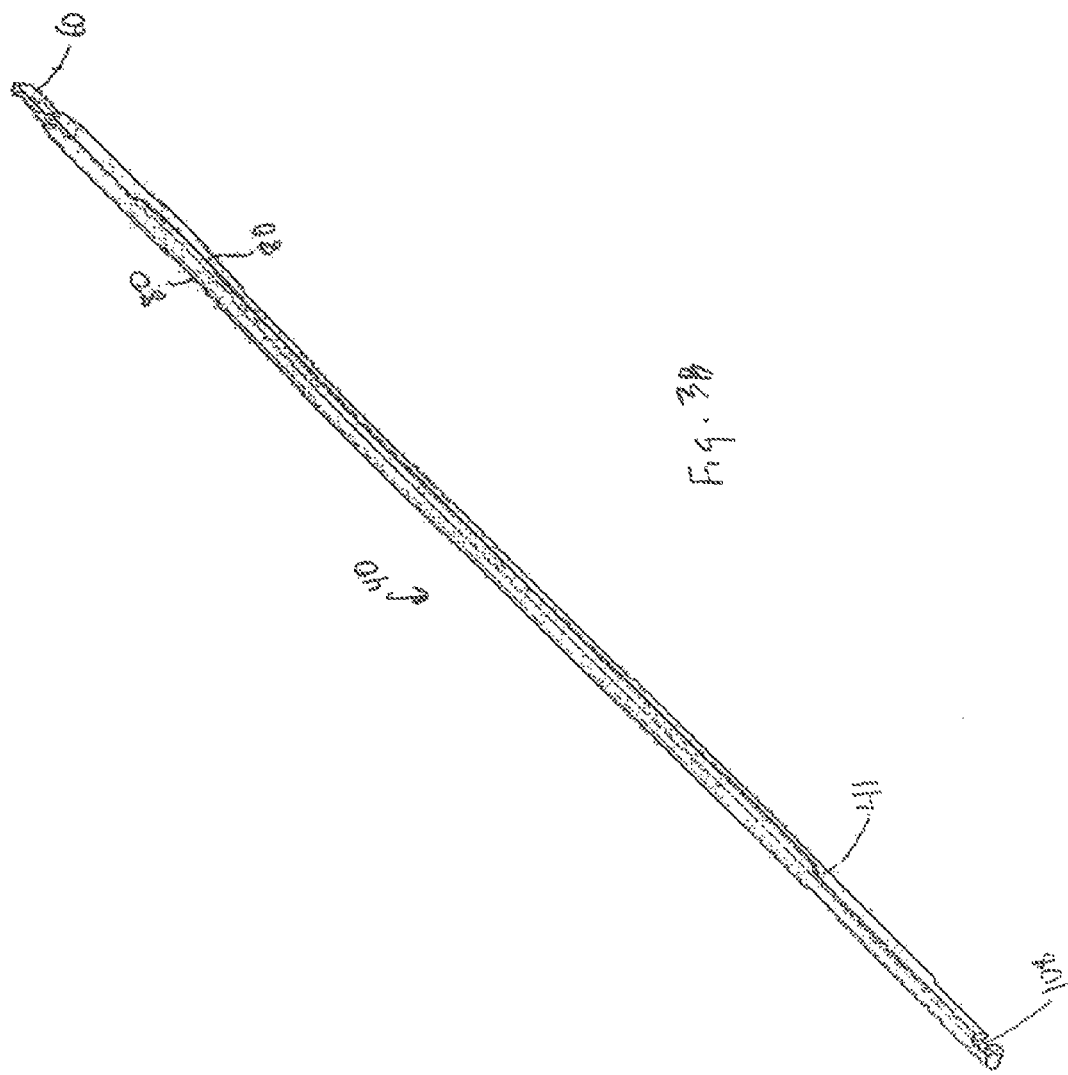

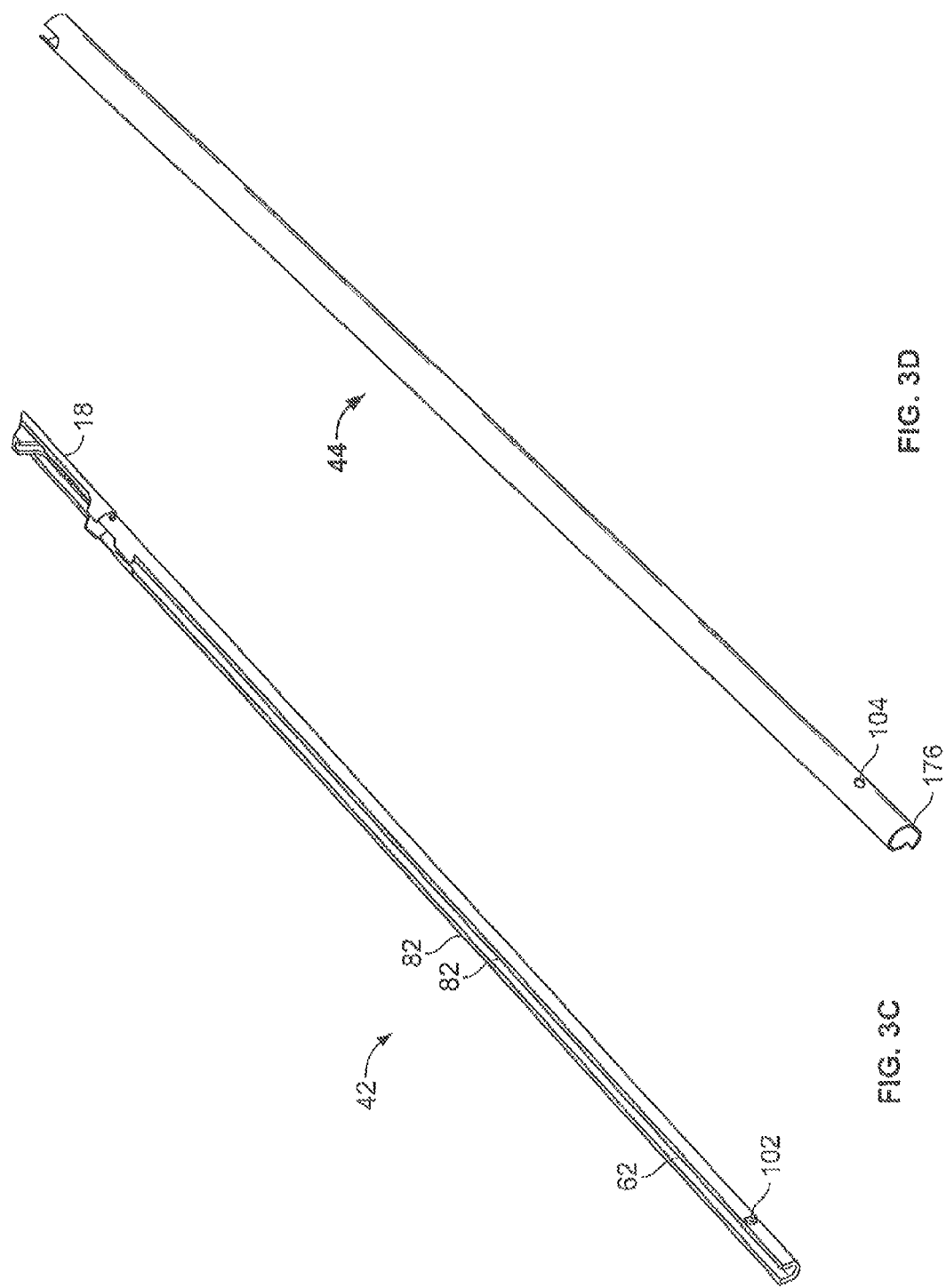

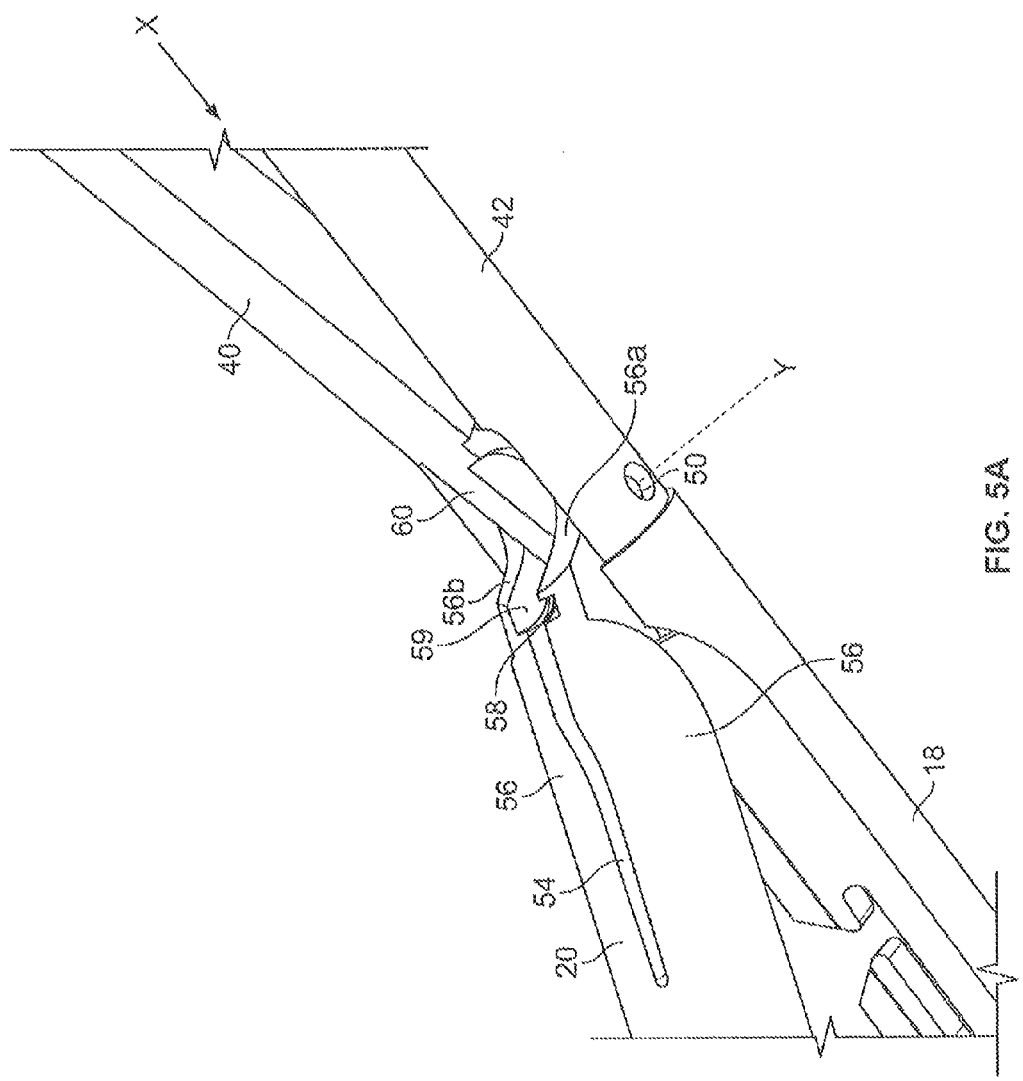

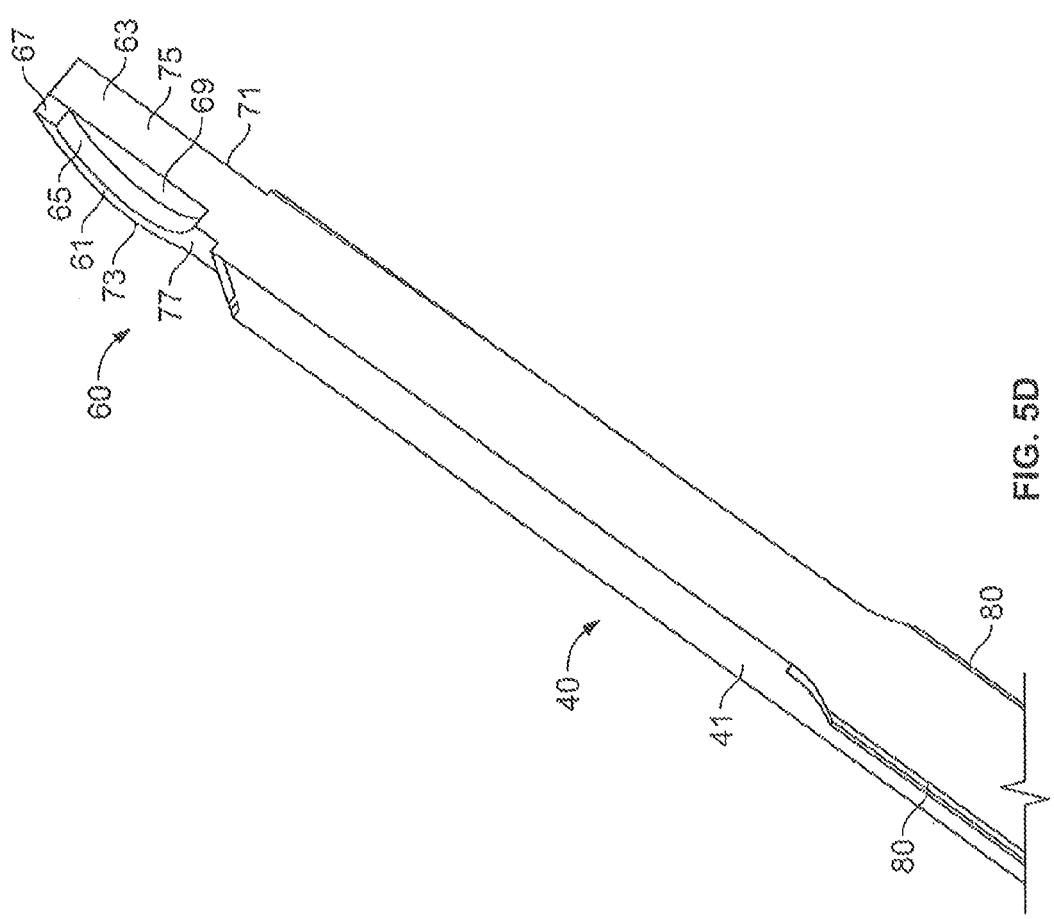

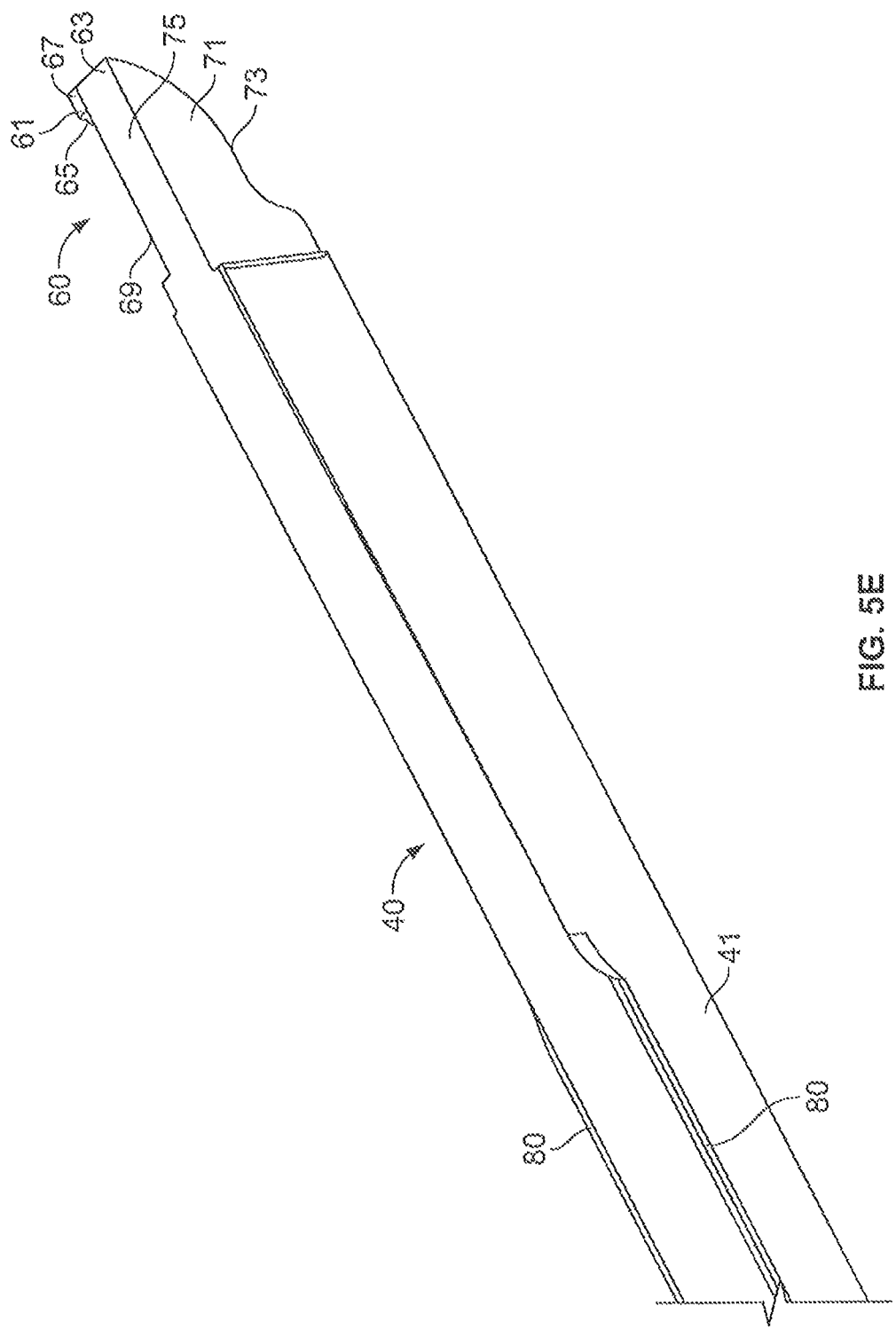

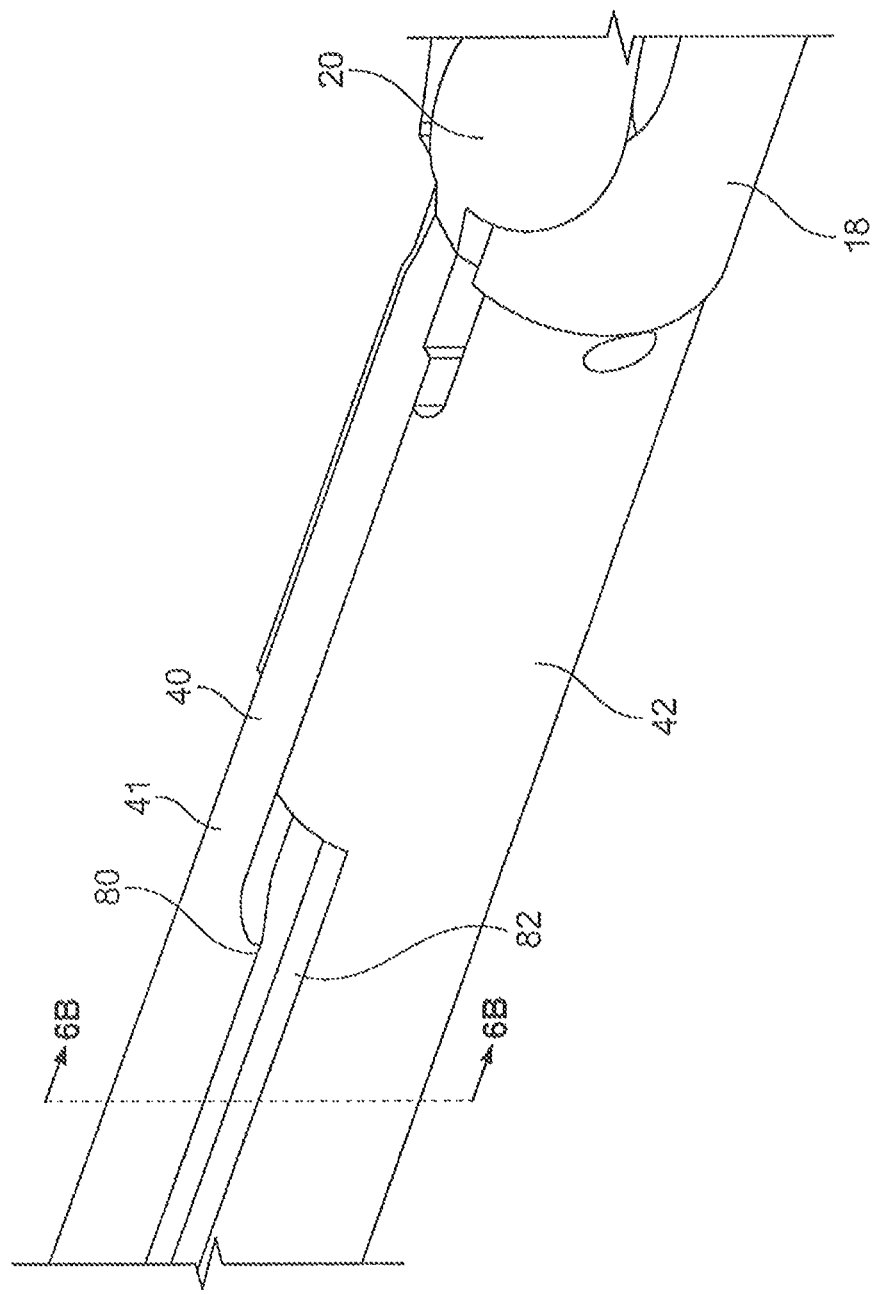

SUTURE PASSING

CROSS-REFERENCE TO RELATED APPLICATIONS

This application is a continuation of U.S. application Ser. No. 11/153,908, filed Jun. 16, 2005, entitled "Suture Passing." U.S. application Ser. No. 11/153,908 claims the benefit of priority of U.S. Provisional Application No. 60/579,682, filed Jun. 16, 2004, entitled "Suture Passing." The entirety of each of the above applications is incorporated herein by reference.

TECHNICAL FIELD

This application relates to suture passing.

BACKGROUND

Surgical procedures, such as soft tissue repair, often encompass passing a suture through tissue, for example to attach soft tissue to bone, to attach soft tissue to soft tissue, or to close a fissure in soft tissue. Instruments for passing suture through tissue are known that include a pair of jaws for grasping the tissue to be sutured. The jaws are used to pass a needle through the tissue.

SUMMARY

In an aspect, a surgical device includes a first member having a pair of opposing projections for receipt in a pair of opposing openings in a second member to enable the first member to pivot relative to the second member about an axis defined by the projections. The first member is deformable to move the projections toward one another such that the projections can be received in the openings.

Implementations of this aspect may include one or more of the following features.

For example, the opposing projections are integral with the first member. The first member defines a slot that enables the first member to deform. The device includes the second member. The first member includes a first jaw body and the second member includes a second jaw body. The first and second jaw bodies are configured to grasp tissue therebetween. The first member defines a contoured surface for mating with an actuating member.

The device further includes the actuating member. The actuating member has a contoured distal portion configured to mate with the contoured surface of the first member such that axial movement of the actuating member pivots the first member. The axial movement of the actuating member is in a direction that is, e.g., substantially perpendicular to the axis defined by the projections.

A stationary member extends from the second member. The stationary member defines a channel that receives the actuating member. The stationary member includes, e.g., wall extending along the channel, and the actuating member includes, e.g., an extension configured to abut against the wall to limit bending of the actuating member when the actuating member is moved to pivot the first member. The actuating member and the stationary member is received in an outer member.

The device includes a handle with a moveable lever coupled to a stationary lever. The moveable lever is coupled to the actuating member to axially move the actuating member to pivot the first member. One of the moveable lever and the stationary lever includes a ratchet and the other of the moveable lever and the stationary lever includes at least one pawl configured to engage the ratchet to releasably lock the levers in one or more positions relative to one another. One of the moveable lever and stationary lever includes a compression spring configured to bias the pawl toward the ratchet. The compression spring can be actuated to release the pawl from the ratchet. The moveable lever is pinlessly coupled to the actuating member by an adaptor configured to translate pivotal movement of the moveable lever into axial movement of the actuating member. The adaptor includes a tube that receives the actuator and that defines a notch for receiving a tab of the moveable lever.

The second member defines a passageway, and the device further includes a needle with a flexible distal portion moveably received in the passageway. The passageway is configured to deflect the distal portion of the needle out of the passageway and toward the first member to pass suture through tissue. A needle actuator is coupled to the needle at a proximal side of the handle. The needle actuator is moveable to move the needle relative to the passageway. A trigger member is coupled to the needle at a distal side of the handle. The trigger member is moveable to move the needle relative to the passageway.

In another aspect, a surgical instrument includes a first pinless joint pivotably coupling a first jaw body to a second jaw body, a second pinless joint coupling a distal portion of an actuating member to the first jaw body, and a third pinless joint coupling a handle to a proximal portion of the actuating member. The third pinless joint translates movement of the handle into axial movement of the actuating member and the second pinless joint translates the axial movement of the actuating member into pivotable movement of the first jaw body relative to the second jaw body about the first pinless joint.

Implementations of this aspect may include one or more of the following. For example, the first pinless joint includes a pair of opposing integral projections on the first jaw body for receipt in a pair of opposing openings in the second jaw body to enable the first jaw body to pivot relative to the second jaw body about an axis defined by the projections. The second pinless joint includes a contoured surface defined in the first jaw body that receives a contoured distal portion of the actuating member. The handle includes a moveable lever coupled to the actuating member by the third pinless joint to translate pivotal movement of the moveable lever into axial movement of the actuating member. The third pinless joint includes a notch for receiving a tab of the moveable lever.

In another aspect, a method of manufacturing a surgical instrument includes pinlessly coupling a first jaw body to a second jaw body for pivotable movement relative to one another; pinlessly coupling a distal portion of an actuating member to the first jaw body such that axial movement of the actuating member is translated into pivotable movement of the first jaw body relative to the second jaw body; and pinlessly coupling a handle to a proximal portion of the actuating member by a such that movement of the handle is translated into the axial movement of the actuating member.

In another aspect, a suture passing instrument includes a housing having a proximal portion and a distal portion. A first jaw and a second jaw are coupled to the distal portion of the housing. The first jaw has an integral pin that is received in a throughbore in the second jaw such that the first and second jaws are pivotable relative to each other. A handle is coupled to the proximal portion of the housing and configured to pivot the jaws. A flexible needle is received in a passageway in one of the first and second jaws. The flexible needle defines an opening for receiving a suture. A needle driver is configured to move the needle relative to the passageway. The jaw that receives the needle is configured to deflect at least a distal portion of the needle out of the passageway and toward the other jaw.

Implementations of this aspect may include one or more of the following features. For example, the first jaw has two integral pins and the second jaw has two throughbores. The second jaw defines a recess and the first jaw defines a slot that forms a pair of spring legs. Each spring leg includes one of the integral pins such that the spring legs can be moved together to fit inside the recess to insert the integral pins into the throughbores. The first jaw further defines a curved groove extending from the slot and the housing includes a moveable member with a curved coupling configured to fit into the groove. The moveable member is moveable by the handle to pivot the first jaw relative to the second jaw. The first and second jaws are pivotable about an axis of the pins.

The housing includes a stationary member defining a channel that receives a moveable member configured to be moved by the handle to pivot the jaws. The stationary member includes, e.g., a wall extending along the channel and the moveable member includes, e.g., an extension configured to abut against the wall to limit bending of the moveable member. The stationary member is connected to one of the jaws. The moveable member is coupled to the other of the jaws. An outer member extends over the stationary member and the moveable member. The moveable member is pinlessly coupled to the handle such that pivotable movement of the handle is translated to linear movement of the moveable member to pivot the jaws.

The needle driver is coupled to a first actuating member and a second actuating member, each of which is configured to move the needle. The first actuating member is configured to be actuated by a thumb of a hand grasping the handle and the second actuating member is configured to be actuated by a different finger. The handle includes a first lever and a second lever pivotable relative to one another. The first lever includes a ratchet and the second lever includes at least one pawl configured to engage the ratchet to releasably lock the levers in one or more positions relative to one another. One of the first and second levers include a compression spring configured to bias the pawl toward the ratchet. The compression spring is actuatable to release the pawl from the ratchet.

In another aspect, a suture passing instrument includes a housing having a proximal portion and a distal portion. A first jaw and a second jaw are coupled to the distal portion of the housing and are pivotable relative to each other. The second jaw defines a recess and the first jaw defines a slot that forms a pair of spring legs such that the spring legs can be moved together to fit inside the recess. A handle is coupled to the proximal portion of the housing and is configured to pivot the jaws. A flexible needle is received in a passageway in one of the first and second jaws. The needle defines an opening for receiving a suture. A needle driver is configured to move the needle relative to the passageway. The jaw that receives the needle is configured to deflect at least a distal portion of the needle out of the passageway and toward the other jaw.

In another aspect, a suture passing instrument includes a housing having a proximal portion and a distal portion. A first jaw and a second jaw are coupled to the distal portion of the housing and are pivotable relative to each other. A handle is coupled to the proximal portion of the housing and is configured to pivot the jaws. A flexible needle is received in a passageway in one of the first and second jaws. The flexible needle defines an opening for carrying a suture. A needle driver is configured to move the needle relative to the passageway. The jaw that receives the needle is configured to deflect at least a distal portion of the needle out of the passageway and toward the other jaw.

Implementations of this aspect may include one or more of the following features. For example, the housing includes a stationary member defining a channel that receives a moveable member configured to be moved by the handle to pivot the jaws. The stationary member includes a wall extending along the channel, and the moveable member includes an extension configured to abut against the wall to limit bending of the moveable member. A needle driver is configured to move the needle relative to the passageway. The needle driver is coupled to a first actuating member and a second actuating member each configured to move the needle. The first actuating member is configured to be actuated by a thumb of a hand grasping the handle and the second actuating member is configured to be actuated by a finger of the hand. The housing includes a moveable member that is pinlessly coupled to the handle such that pivotable movement of the handle is translated to linear movement of the moveable member to pivot the jaws.

Advantages may include ease of assembly, a limitation on the number of moving parts, reduced manufacturing cost, and increased durability.

The details of one or more implementations are set forth in the accompanying drawings and the description below. Other features will be apparent from the description and drawings, and from the claims.

BRIEF DESCRIPTION OF THE DRAWINGS

FIG. 2A shows the suture passing instrument of FIG. 1 with a needle extending from a distal end of the instrument;

FIG. 2B is an enlarged view of section 2B of FIG. 2A;

FIG. 3B shows an upper jaw actuator of the suture passing instrument of FIG. 1;

FIG. 3C shows a lower jaw shaft of the suture passing instrument of FIG. 1;

FIG. 3D shows an outer tube of the suture passing instrument of FIG. 1;

FIG. 5A shows the distal portion of the lower jaw shaft and the upper jaw actuator of the suture passing instrument of FIG. 1 during assembly with the upper jaw;

FIGS. 5D and 5E are close up perspective views of the distal portion of the upper jaw actuator of FIG. 3B.

FIG. 6A shows the assembled lower jaw shaft, upper jaw actuator, and upper jaw of the suture passing instrument of FIG. 1;

DETAILED DESCRIPTION

Figure 1:
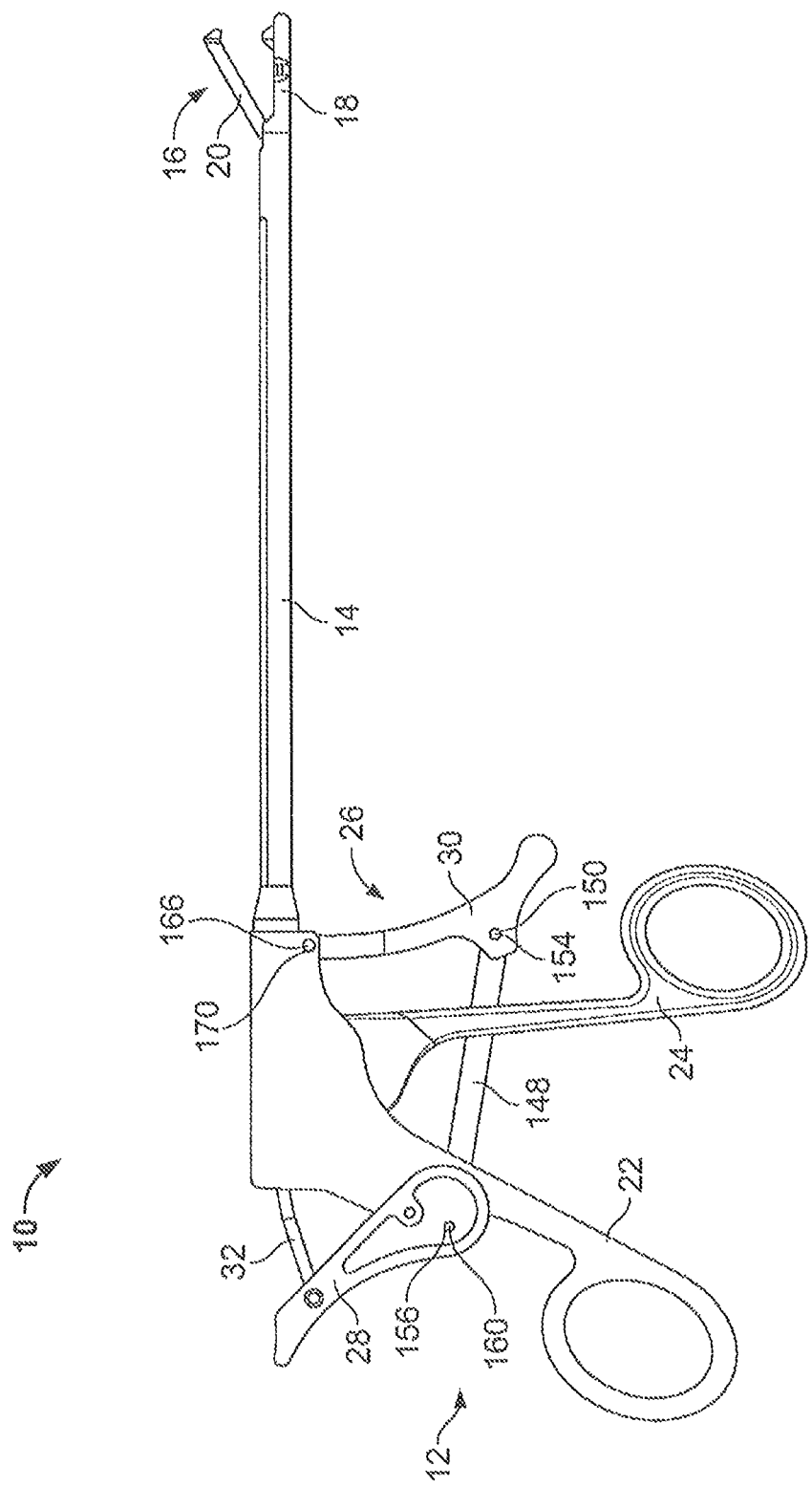
FIG. 1 is an illustration of a suture passing instrument.
Figure 3A:
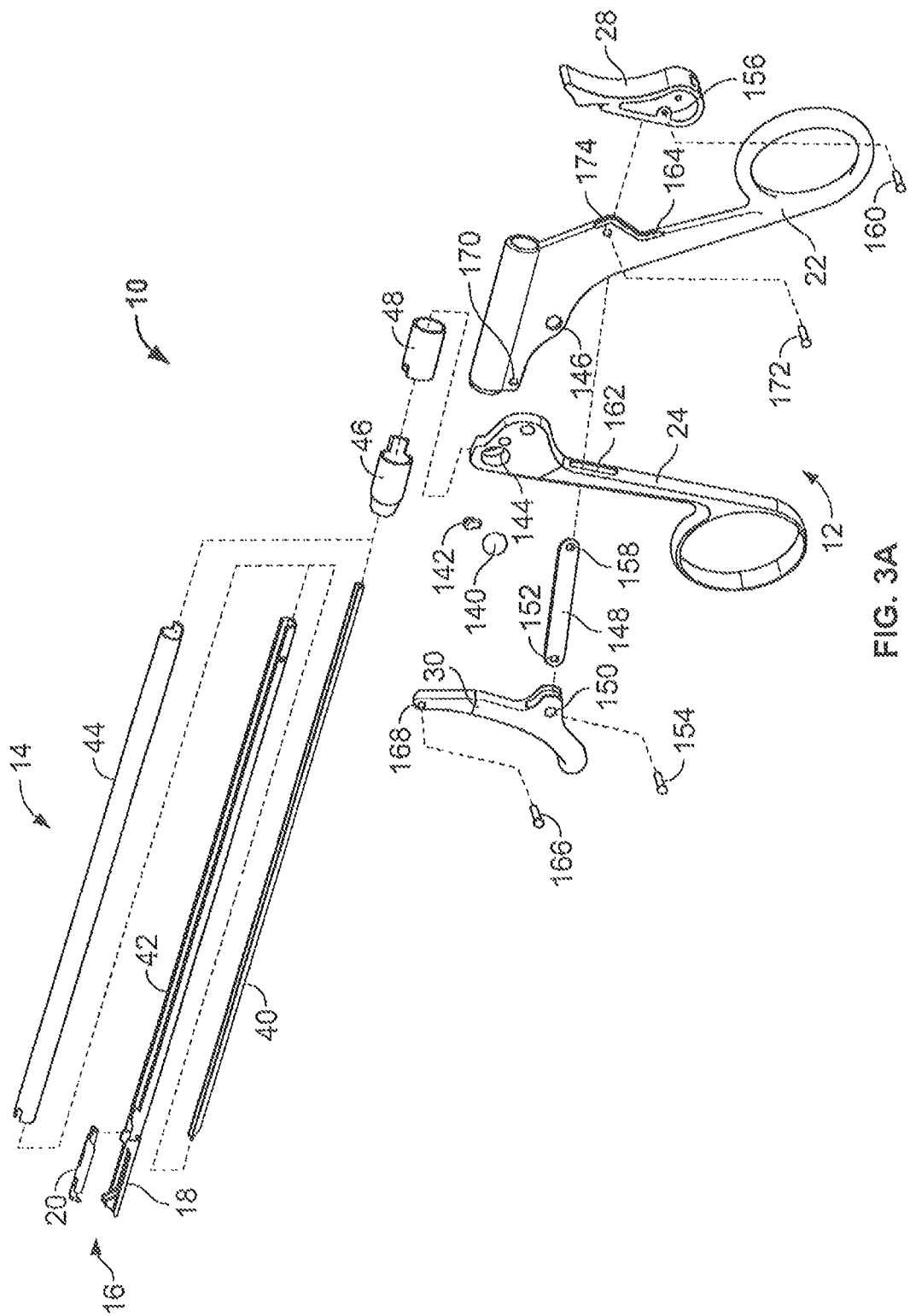
FIG. 3A is an exploded view of the suture passing instrument of FIG. 1 without the needle.

Referring to FIG. 1, a suture passing instrument 10 includes a handle 12, an elongated housing 14, and a distal jaw assembly 16. Jaw assembly 16 includes a first member in the form of a moveable jaw 20 and a second member in the form of a stationary jaw 18. The moveable jaw 20 is pivotable relative to the stationary jaw 18. Handle 12 includes a stationary lever in the form of a thumb loop 22 and a moveable lever in the form of a finger loop 24 that is movable relative to thumb loop 22 to open and close jaw 20. Handle 12 includes a needle actuating assembly 26 with a linked thumb needle driver 28 and a finger trigger 30. Referring also to FIGS. 2A and 2B, slidably received within housing 14 and attached to needle driver 28 is a needle 32 used to pass a suture through tissue.

Referring to FIGS. 3A-3D, housing 14 is formed by an upper jaw actuator 40, a lower jaw shaft 42 (of which jaw 18 forms the distal portion), and an outer tube 44 within which actuator 40 and lower jaw shaft 42 are received. As discussed further below, lower jaw shall 42 and outer tube 44 are attached to a tube adapter 46, and actuator 40 extends through tube adapter 46 and attaches to an actuator link 48. Tube adapter 46 and actuator link 48 are received within thumb loop 22, with tube adapter 46 being fixed to thumb loop 22, and actuator link 48 being movable relative to thumb loop 22. Finger loop 24 is pinlessly attached to actuator link 48, as described below, such that pivotal movement of finger loop 24 moves actuator link 48, which moves upper jaw actuator 40 axially to open and close jaw 20.

Figure 4:
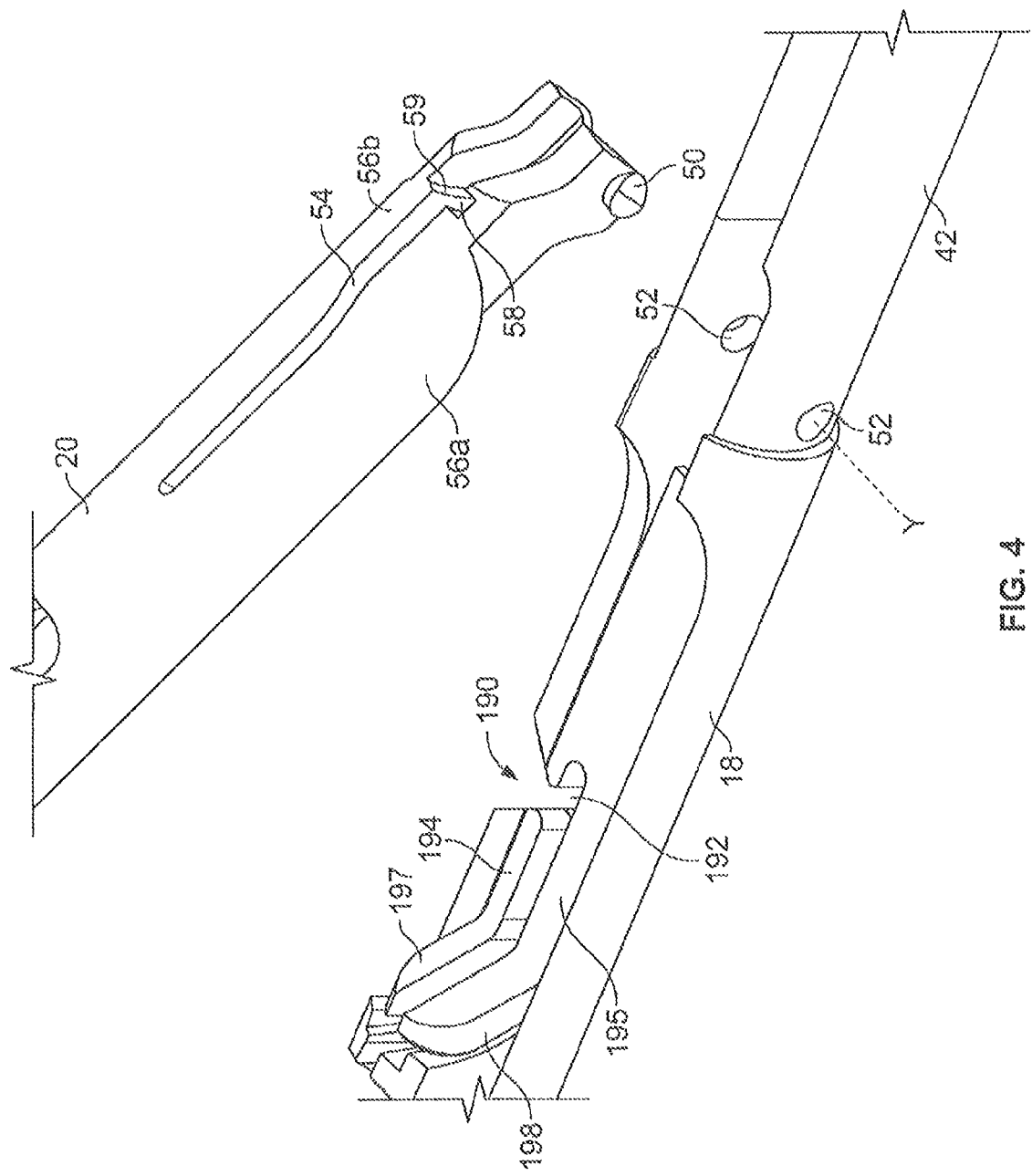
FIG. 4 is an exploded view of the distal portion of the lower jaw shaft and an upper jaw of the suture passing instrument of FIG. 1.

Referring to FIG. 4, jaw 20 is pinlessly coupled to jaw 18 by a pair of integrally molded or machined projections 50 (only one projection 50 is shown in FIG. 4) that are respectively received in two openings 52 defined in jaw 18. Jaw 20 defines a slot 54 that forms two spring legs 56*a*, 56*b* such that legs 56*a*, 56*b* can be compressed together when jaw 20 is being loaded into lower jaw shaft 42. When legs 56*a*, 56*b* are released, projections 50 move into holes 52 to couple jaw 20 to jaw 18.

Figure 5B:
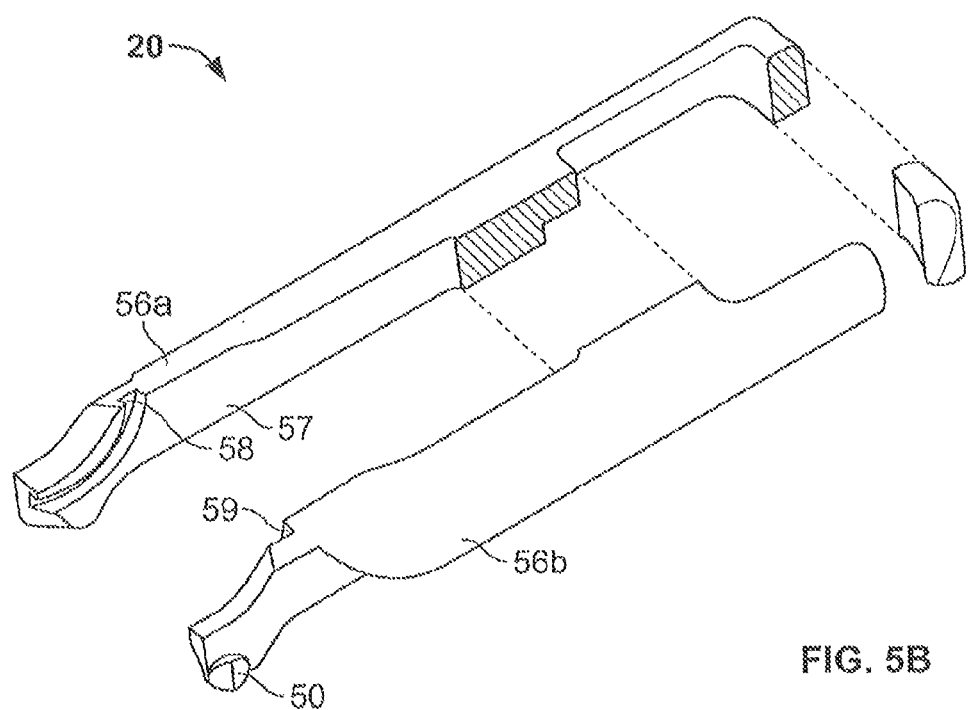
FIGS. 5B and 5C are close up perspective views of the upper jaw of the suture passing instrument of FIG. 1, split along the slot in the upper jaw.
Figure 5C:
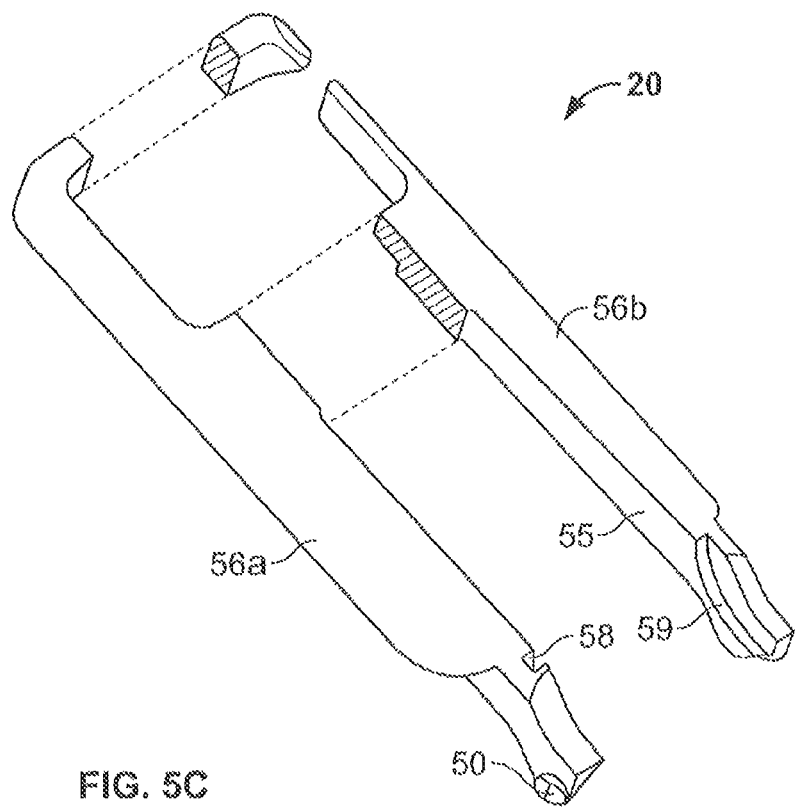

Referring to FIG. 5A, jaw 20 is pinlessly coupled to actuator 40 such that axial movement of actuator 40 in direction X translates to pivotal movement of jaw 20 about an axis Y defined by projections 50, which is substantially perpendicular to axis X (FIG. 5A shows actuator 40 out of its normal position received in lower, jaw shaft 42). Referring also to FIGS. 5B and 5C, jaw 20 defines a contoured surface in the form of a curved lug groove 58 formed in an interior wall 57 of leg 56*a* and a correspondingly curved ledge 59 formed in an interior wall 55 of leg 56*b*. Referring also to FIGS. 5D and 5E, actuator 40 includes a distal coupling 60 having an extension 63 that is received in slot 54, and a curved lug 61 (shown shaded) that is received in groove 58. Extension 63 is defined by a top wall 75, parallel side walls 69 and 71 and a curved bottom wall 73 with a curvature that corresponds to the curvature of curved ledge 59 such that with extension 63 received in slot 54 bottom wall 73 abuts ledge 59. Lug 61 extends from side wall 69 and is defined by curved bottom wall 73, a curved top wall 65, a side wall 77, and an end wall 67 that extends from top wall 75 of extension 63. The curvature of lug 61 corresponds to the curvature of lug groove 58. This pinless coupling formed between actuator 40 and jaw 20 transmits axial movement of actuator 40 into pivotal movement of jaw 20 to open and close jaw 20, e.g., as described in U.S. Pat. No. 4,712,545, which is hereby incorporated by reference in its entirety. Distal coupling 60 of actuator 40 also limits movement of legs 56*a* and 56*b* toward one another, which limits any tendency of jaw 20 to release from lower jaw shaft 42.

Referring to FIGS. 3B, 3C, 6A, and 6B, lower jaw shaft 42 defines a channel 62 having a generally U-shaped cross-section for receiving actuator 40. Lower jaw shaft 42 has two walls 82 and actuator 40 has a body 41 with two laterally extending extensions 80 that are normally spaced from walls 82 and from outer tube 44. When a heavy load is applied to actuator 40, causing actuator 40 to bend, contact between extensions 80 and walls 82 or outer tube 44 limits any tendency of actuator 40 to collapse inside lower jaw shaft 42. With actuator 40 placed in channel 62, body 41 of actuator 40 is spaced from a lower surface 84 of the channel 62 such that actuator 40 and lower jaw shaft 42 define a longitudinally extending slot 43 therebetween for receiving needle 32. Referring also to FIG. 7, upper jaw actuator 40 and lower jaw shaft 42 are received within outer tube 44 such that actuator 40 is held within channel 62 in lower jaw shaft 42.

Figure 9:
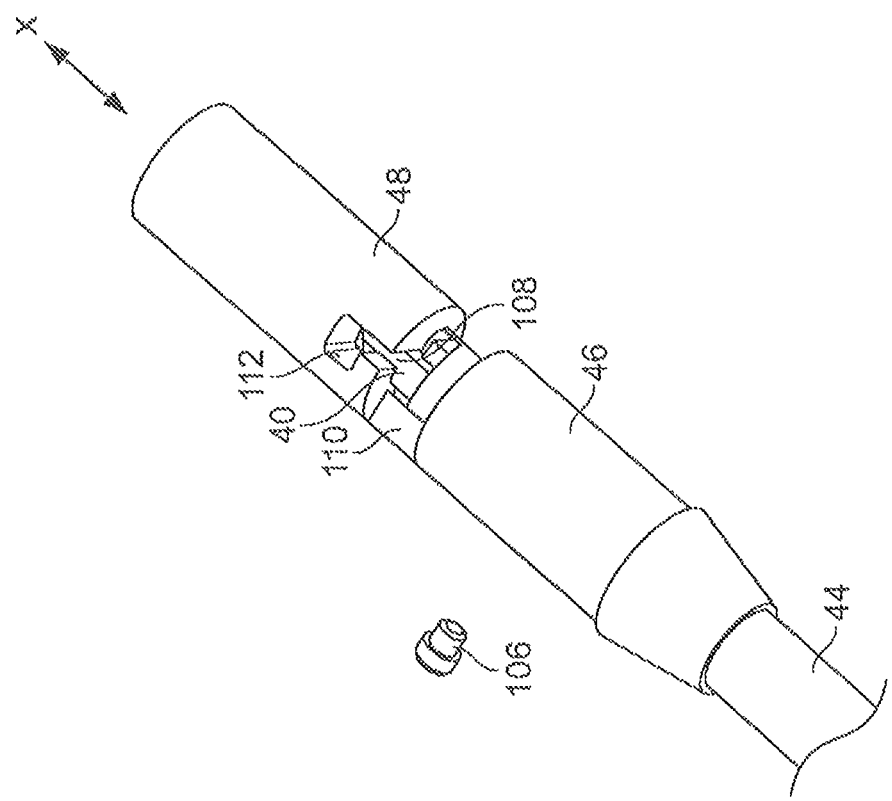
FIG. 9 is an illustration of the coupling of the upper jaw actuator to an actuator link of the suture passing instrument of FIG. 1.

Referring to FIGS. 3A-3D and 8, tube adapter 46 defines a threaded hole 100, and lower jaw shaft 42 and outer tube 44 each define a counterbore 102, 104, respectively, that are aligned with hole 100 during assembly. To attach lower jaw shaft 42 and tube 44 to adapter 46, a screw 106 is threadedly received within hole 100 and extends into counterbores 102, 104. Upper jaw actuator 40 has a proximal, L-shaped extension 108 that extends beyond the proximal end 110 of tube adapter 46. Referring also to FIG. 9, actuator link 48 defines a corresponding notch 112 for receiving extension 108 such that axial movement of link 48 moves actuator 40 axially in direction X. Proximal end 110 of tube adapter 46 acts to limit the extent to which actuator link. 48 can be advanced distally, and thus limits the closing force that can be applied to jaw 20.

Figure 10:
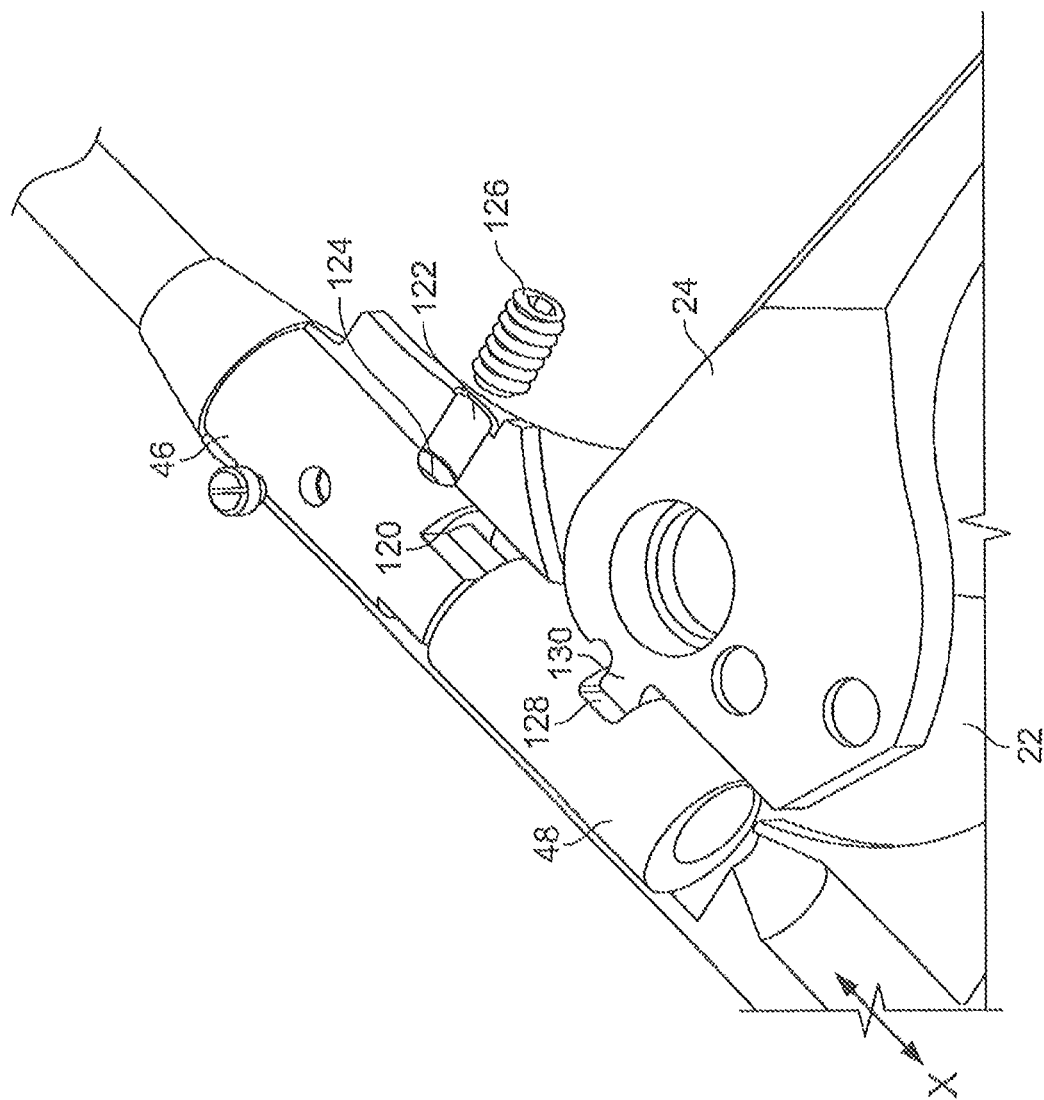
FIG. 10 illustrates the coupling of the tube adapter and actuator link to a handle of the suture passing instrument of FIG. 1.

Referring to FIG. 10, tube adapter 46 and actuator link 48 are received within a bore 120 in thumb loop 22. Thumb loop 22 defines a threaded hole 122 and adapter 46 defines a counterbore 124 that is aligned with bore 122 during assembly. Adapter 46 is fixed in position relative to stationary thumb loop 22 by a screw 126 that is threaded into hole 122 and received with counterbore 124. Finger loop 24 is pinlessly coupled to actuator link 48 to transmit pivotal movement of finger loop 24 to axial movement of actuator link 48 to open and close jaw 20. Actuator link 48 defines a notch 128 and finger loop 24 has a tab 130 received in notch 128 such that pivotal movement of finger loop 24 moves actuator link 48 axially in direction X.

Referring again to FIGS. 1 and 3A, finger loop 24 of handle 12 is held within thumb loop 22 of handle 12 by a button 140 and spring 142, received within openings 144 and 146, as is conventional in the art. Trigger 30 is positioned on a distal side of handle 12 and needle driver 28 is positioned on a proximal side of handle 12. Trigger 30 and needle driver 28 are coupled by a trigger link 148 that is received within slots 162, 164 defined in finger loop 24 and thumb loop 22, respectively, so that trigger 30 and needle driver 28 are moveable together to actuate needle 32. Trigger 30 defines holes 150 and trigger link 148 defines a hole 152 for receiving a pin 154 that pivotally attaches trigger 30 to trigger link 148. Needle driver 28 defines holes 156 and trigger link 148 defines a hole 158 for receiving a pin 160 that pivotally attaches needle driver 28 to trigger link 148. Trigger 30 is pivotally coupled to thumb loop 22 by a pin 166 received in holes 168, 170, defined in trigger 30 and thumb loop 22, respectively. Needle driver 28 is pivotally coupled to thumb loop 22 by a pin 172 received within holes 174 in thumb loop 22 and within detents (not shown) in an inner surface of needle driver 28.

Figure 6B:
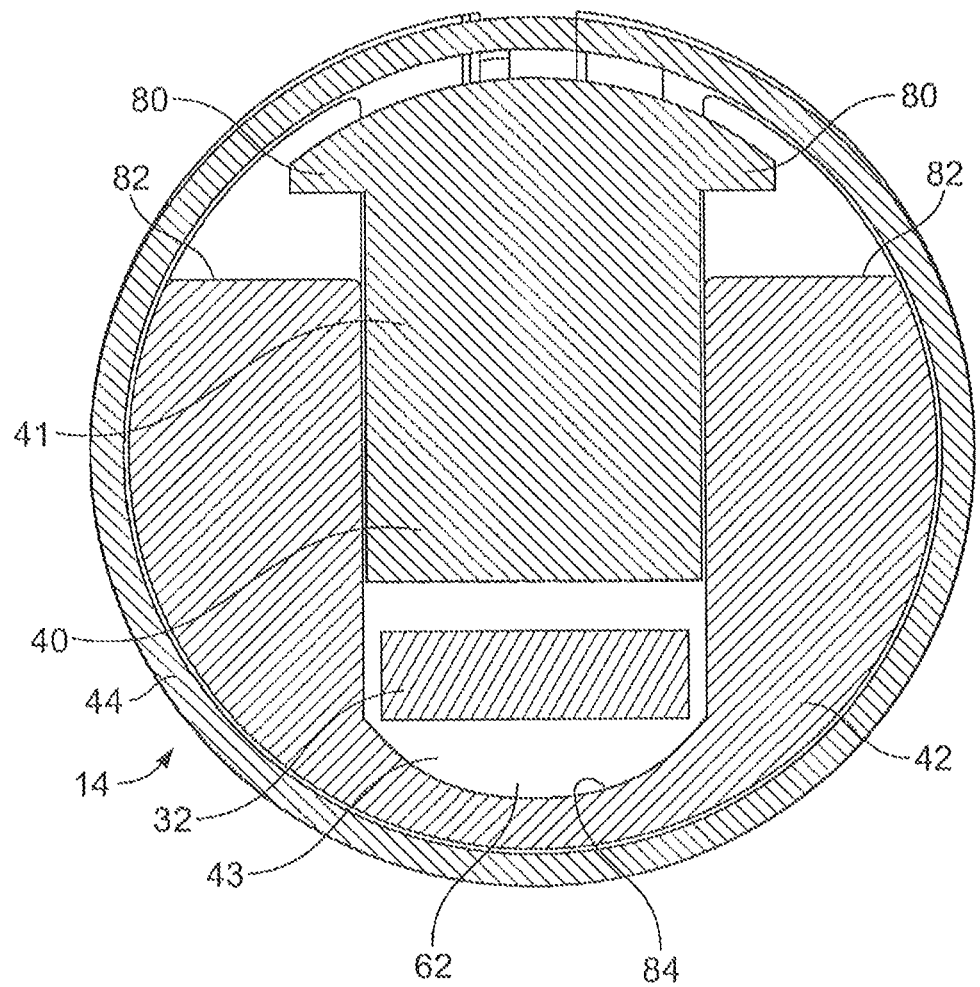
FIG. 6B shows a cross-sectional view of the assembled lower jaw shaft and upper jaw actuator taken along line 6B-6B in FIG. 6A.
Figure 7:
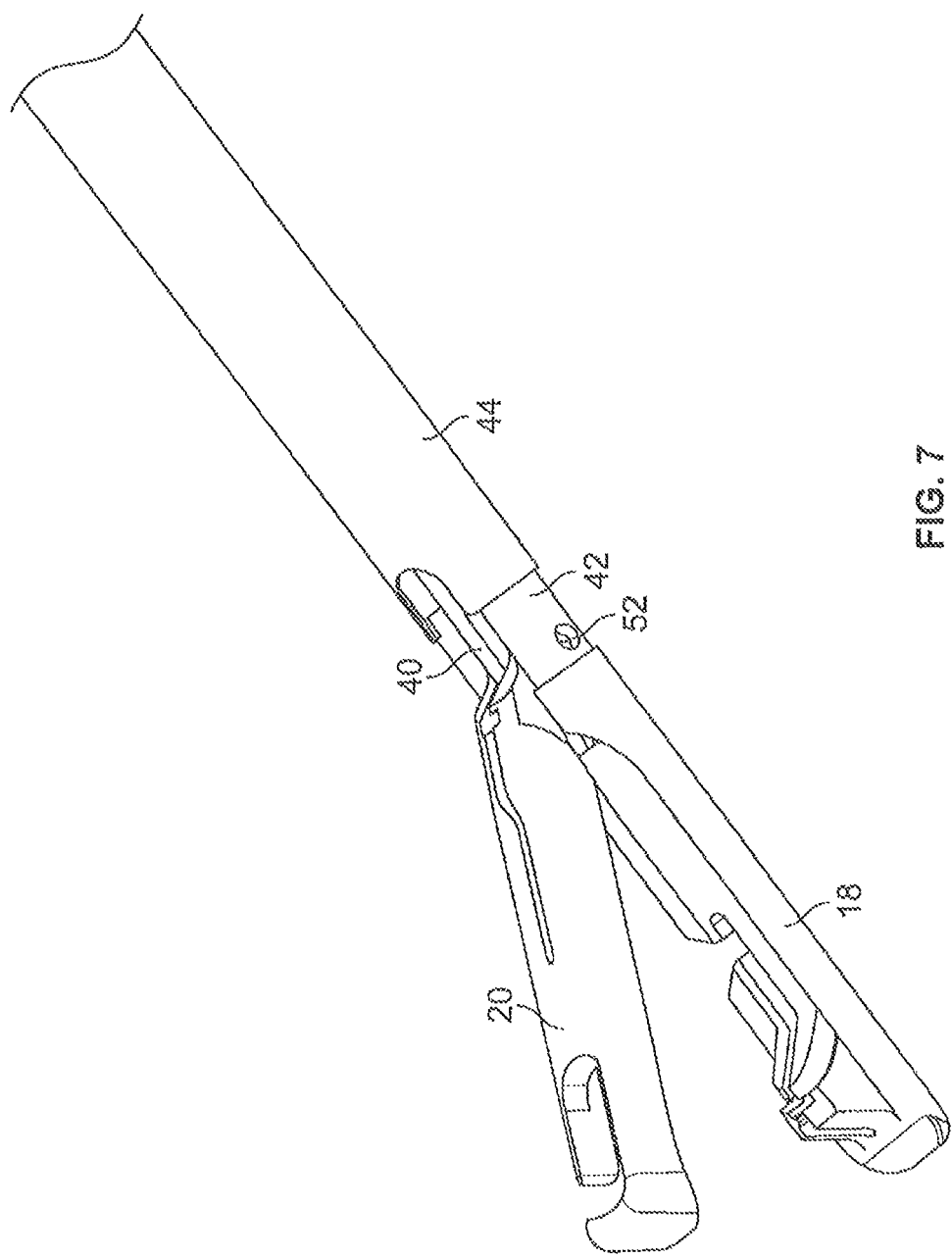
FIG. 7 is an illustration of the distal portion of the suture passing instrument of FIG. 1 showing the outer tube placed over the lower jaw shaft and upper jaw actuator.
Figure 8:
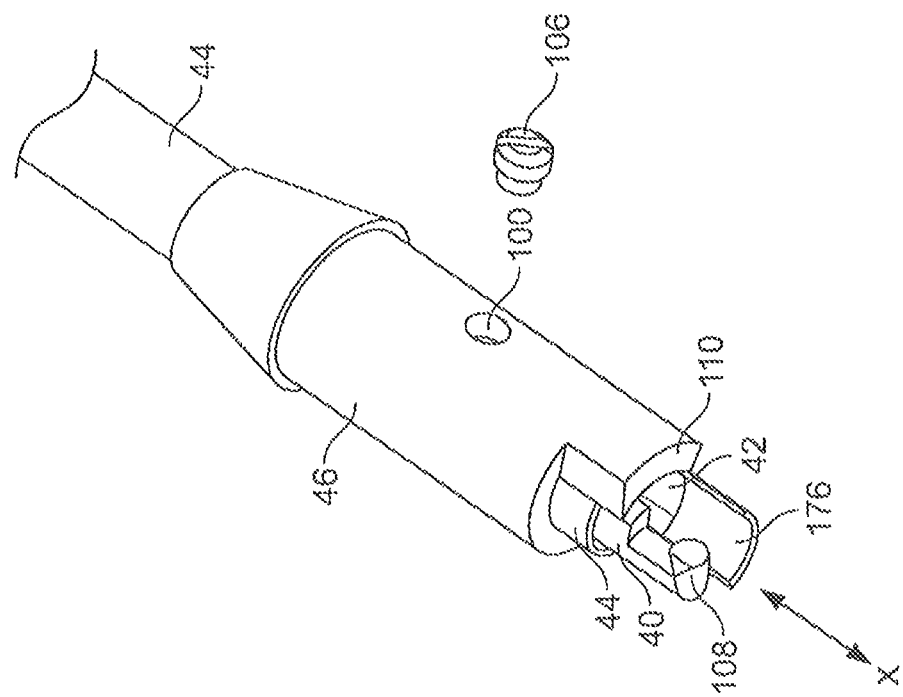
FIG. 8 is an illustration of the coupling of the upper jaw actuator, lower jaw shaft, and outer tube to a tube adapter of the suture passing instrument of FIG. 1.
Figure 11:
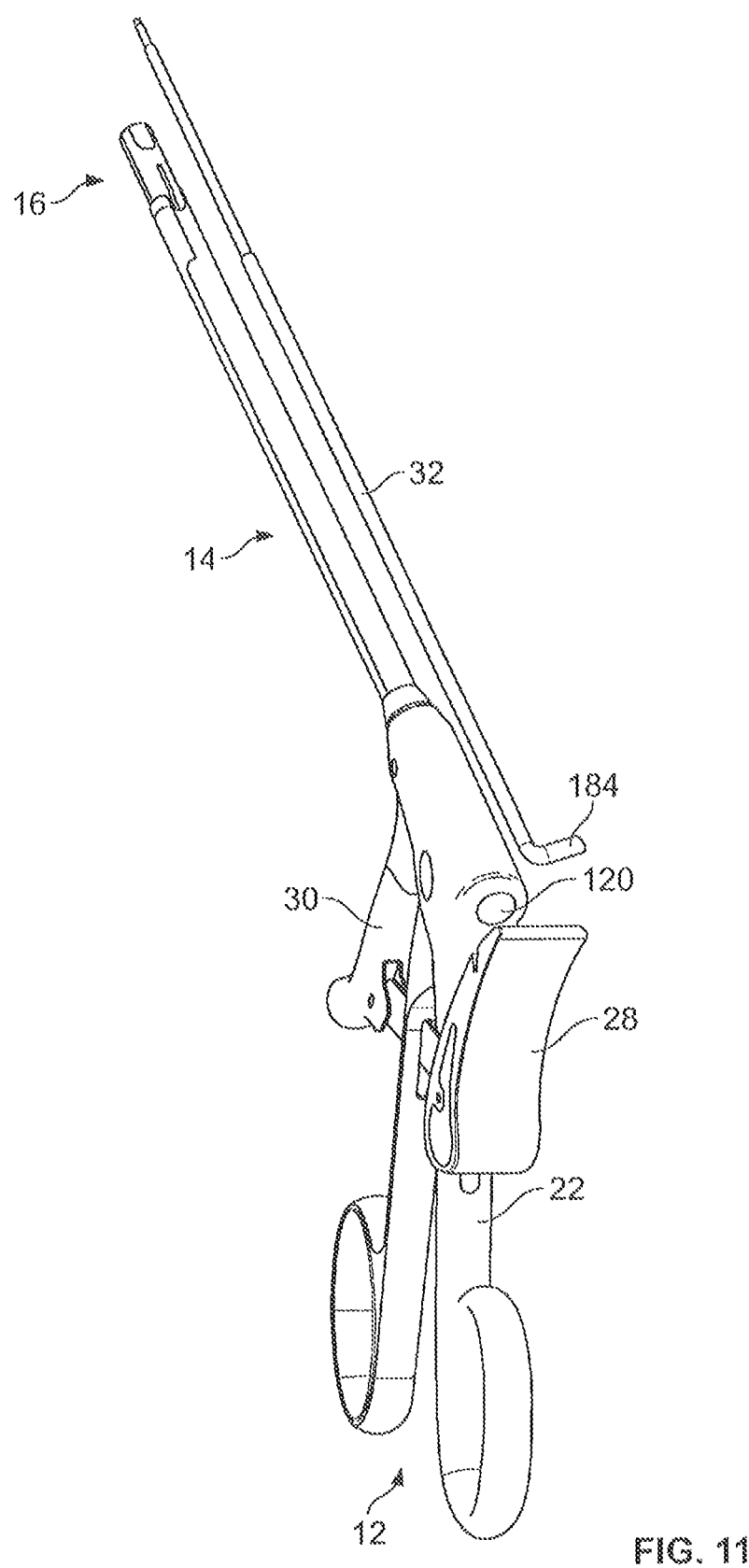
FIG. 11 is an illustration of the suture passing instrument of FIG. 1 with the needle prior to loading of the needle.
Figure 12:
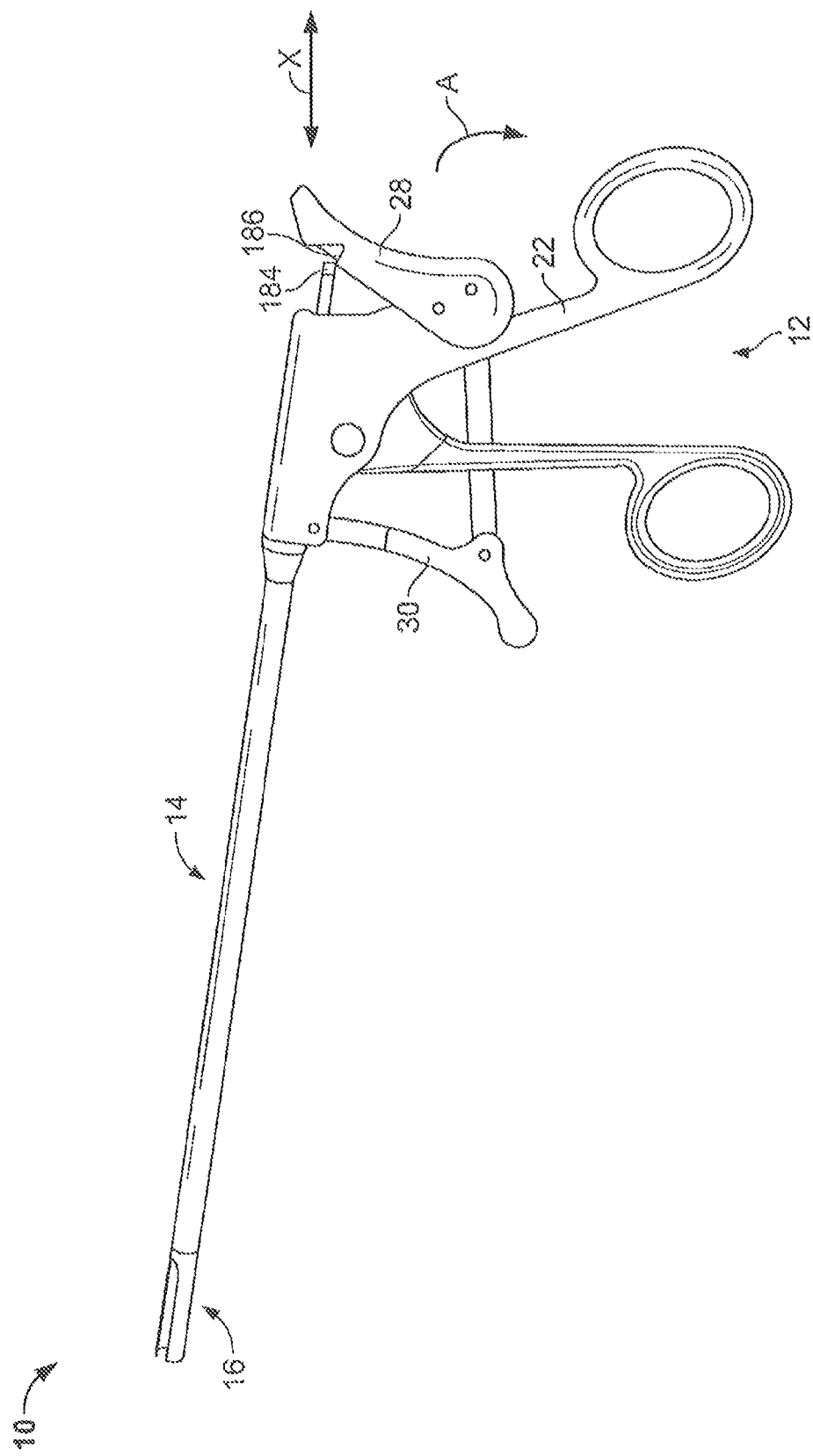
FIG. 12 is an illustration of the suture passing instrument of FIG. 1 with the needle loaded.

Referring to FIGS. 6B and 11, needle 32, formed, e.g., of nitinol wire, is received within bore 120 in thumb loop 22, and extends distally within housing 14 in the slot 43 between actuator 40 and lower jaw shaft 42. Referring also to FIGS. 3D and 8, tube 44 includes a tab 176 that helps guide needle 32 during introduction into the slot. Needle 32 has a proximal bend, e.g., at approximately a right angle, forming a needle driver link 184. Referring also to FIG. 12, needle driver link 184 is received within a hole 186 defined in needle driver 28 such that movement of needle driver 28 or trigger 30 moves needle 32 back and forth within housing 14 in direction X. To position needle 32 within housing 14, needle driver 28 is pivoted away from thumb loop 22, in the direction of arrow A, such that there is a clear path for introduction of needle 32 into bore 120 in thumb loop 22. The proximal end of the needle is then bent slightly such that needle driver link 184 can be placed in hole 186.

Referring also to FIGS. 2A, 2B, 4, and 6B, needle 32 has a flexible distal portion 181 with a pointed distal end 180, an edge 196, and a suture receiving slot 182 extending proximally from edge 196 for receiving a suture thread. Lower jaw 18 includes a body portion 195 and a ramp portion 197 that together define a passageway 198 for receiving needle 32. When needle driver 28 is moved in the direction of arrow C and/or trigger 30 is moved in the direction of arrow D, needle 32 is advanced distally through passageway 198 in the direction of arrow C. As shown in FIG. 2B, body portion 195 and ramp portion 197 deflect distal portion 181 of needle 32 out of passageway 198 and toward the jaw 20 so that needle 32 can pass suture through tissue.

Figure 13:
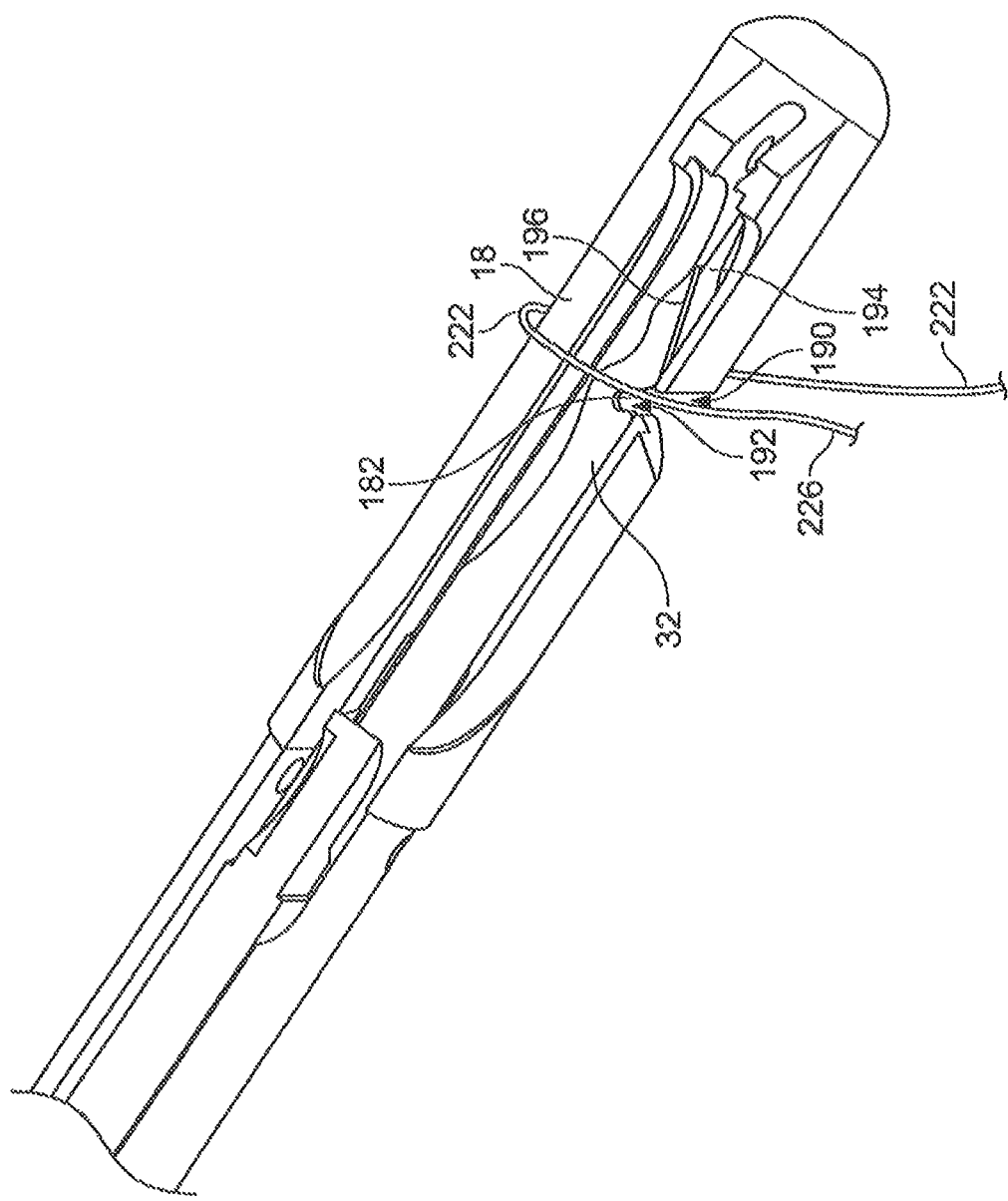
FIG. 13 is an illustration of the distal portion of the suture passing instrument of FIG. 1 showing the needle in a suture loading position.
Figure 14:
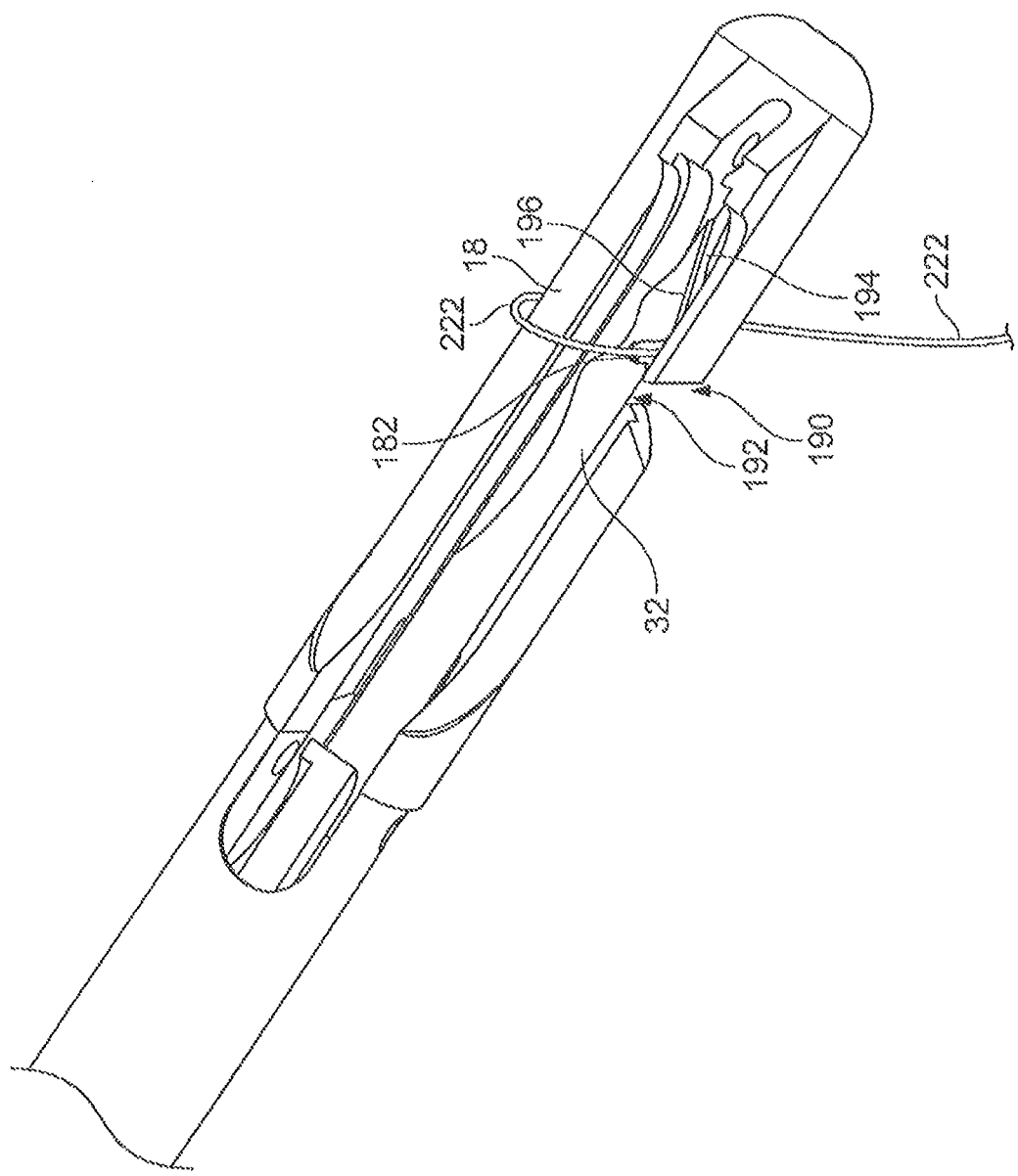
FIG. 14 is an illustration of the distal portion of the suture passing instrument of FIG. 1 showing the needle in a rest position.

Referring to FIGS. 4 and 13, jaw 18 defines a side suture receiving slot 190 that leads to a longitudinal suture receiving slot 192. Needle 32 can be positioned with needle slot 182 and jaw slot 190 aligned such that a suture thread 222 can be passed through slot 190 into slot 182. Referring to FIG. 14, when needle 182 is advanced distally, suture 222 extends through slot 192 and is trapped between needle 32 and jaw 18. Jaw 18 includes a ledge 194 that supports edge 196 of the needle 32 during advancement and retraction of needle 32.

As shown for example in FIG. 2B, jaw 20 includes a cut-out 210 and a slot 212 leading to cut out 210 that form a hook-shaped distal end 214 on jaw 20. Needle 32 freely passes through hook shaped distal end 214 when needle is advanced from jaw 18 to pass suture through tissue. After the suture is passed through the tissue, needle 32 is retracted into jaw 18, leaving the suture in the tissue. The passed suture can be further manipulated by hook-shaped distal end 214, e.g., by placing hook shaped distal end 214 through a loop in the suture and pulling the suture away from the tissue.

Figure 15:
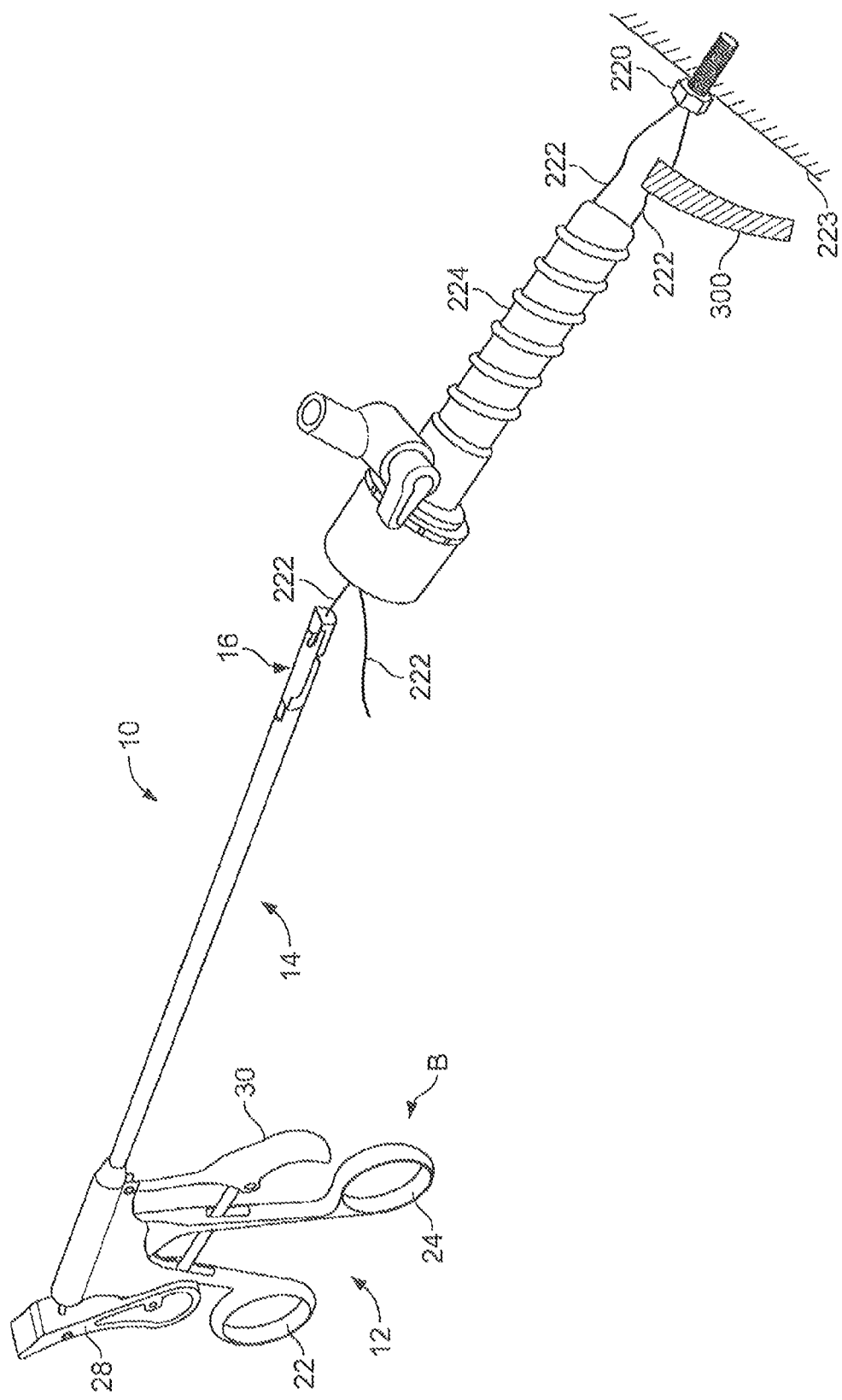
FIGS. 15-18 shows the suture passing instrument of FIG. 1 in use.
Figure 16:
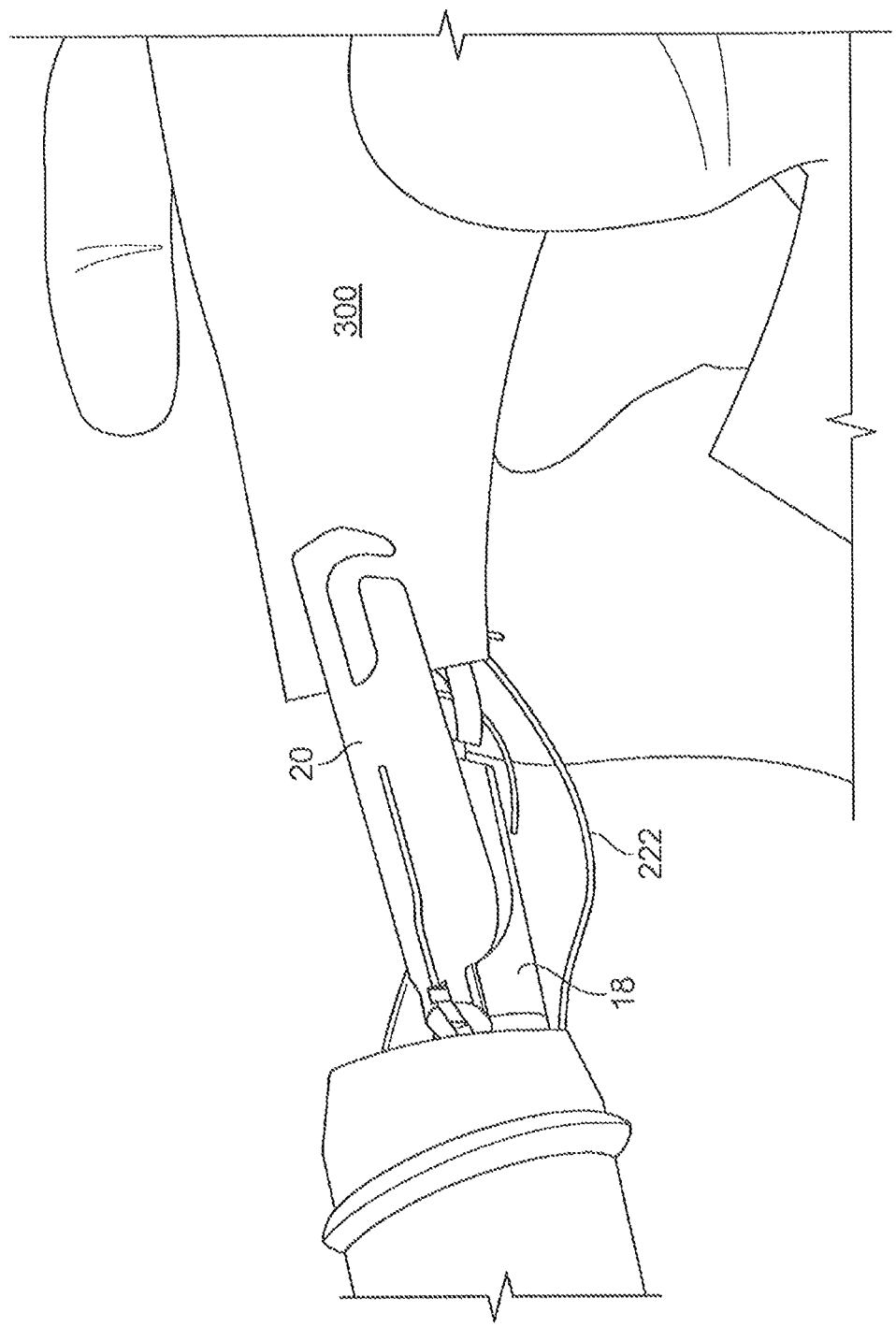

Referring to FIG. 15, in use, e.g., in attaching a soft tissue 300 to bone 223, after placing a suture anchor 220 and attached suture 222, e.g., a braided U.S.P. #0 to #2 suture, into bone 223 in a joint, e.g., the shoulder joint, through a cannula 224, e.g., a 5.5 mm cannula, with the suture 222 extending from the anchor 220 through the cannula 224 to the outside of the joint, the suture 222 is loaded into instrument 10. To load the suture 222, with jaw 20 open, the operator moves needle driver 28 in the direction of arrow A (FIG. 12) to align suture slots 190, 182 (FIG. 13). The operator then loops suture 222 over jaw 18 (FIG. 13) and passes the free end portion 226 of suture 222 through slot 190 into slot 182. The movement of needle driver 28 in the direction of arrow A (FIG. 12) creates a slight bend in needle 32, biasing needle distally, such that when needle driver 28 is released, the needle 32 and needle driver 28 automatically return to their rest position, corresponding to the position of needle 32 shown in FIG. 14. Ramp portion 197 (FIG. 2B) prevents needle 32 from traveling distally beyond the rest position when needle driver 28 is released. The operator then closes jaw 20 by moving finger loop 24 in the direction of arrow B, and advances instrument 10 through the cannula to the surgical site. The operator then opens jaw 20 and manipulates instrument 10 such that tissue 300 to be reattached to the bone is positioned between jaws 18 and 20. The operator then closes jaw 20 to grasp tissue 300 (FIG. 16).

Figure 17:
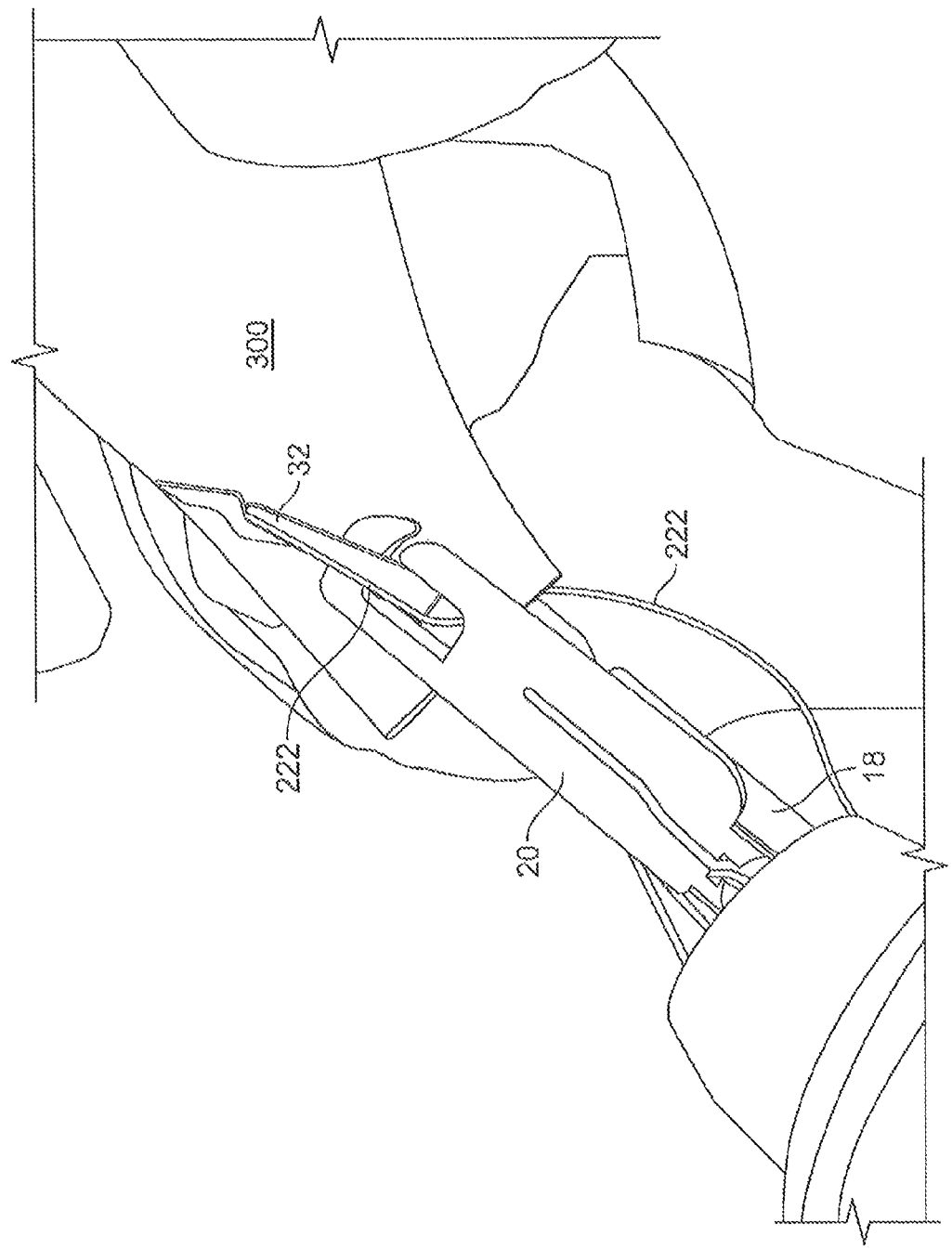
Figure 18:
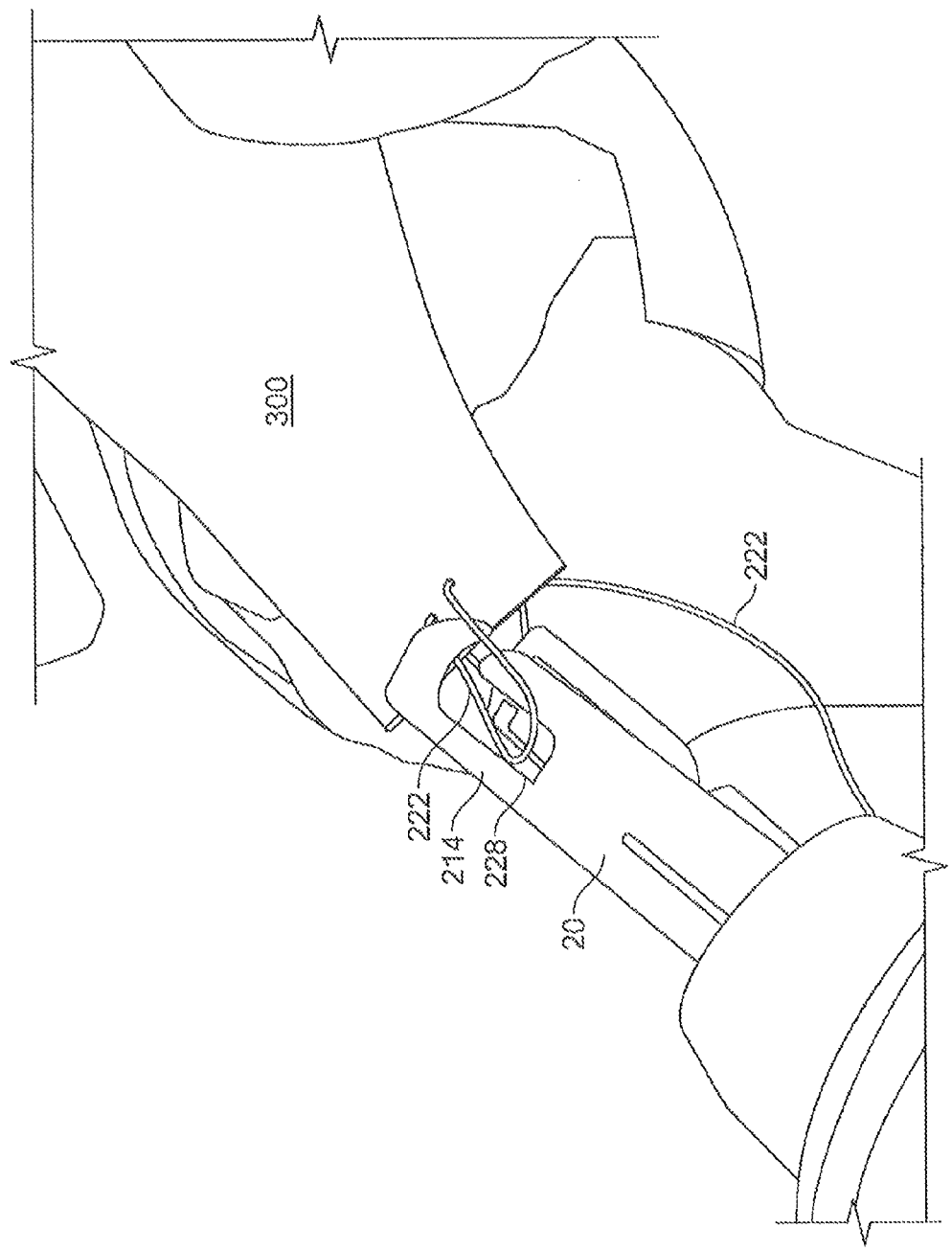

Referring to FIG. 17, with tissue 300 secured between jaws 18, 20, the operator advances needle 32 through tissue 300, either by pushing on needle driver 28 (arrow C, FIG. 2A) or pulling on trigger 30 (arrow D, FIG. 2A). Referring to FIG. 18, the operator then reverses the movement of needle driver 28 or trigger 30 to retract needle 32 to its rest position, leaving a loop 228 of suture 222 extending through tissue 300. The operator opens jaw 20 releasing tissue 300, and places hook 214 of jaw 20 through loop 228 of suture 222. (Alternatively, a separate grasping instrument can be used.) To complete the procedure, the operator closes jaw 20, pulls instrument 10 with captured suture 222 through cannula 224, and ties off the suture 222 to re-approximate tissue 300 to bone. Instrument 10 is, for example, reusable with the exception of needle 32, which is disposable.

Figure 19:
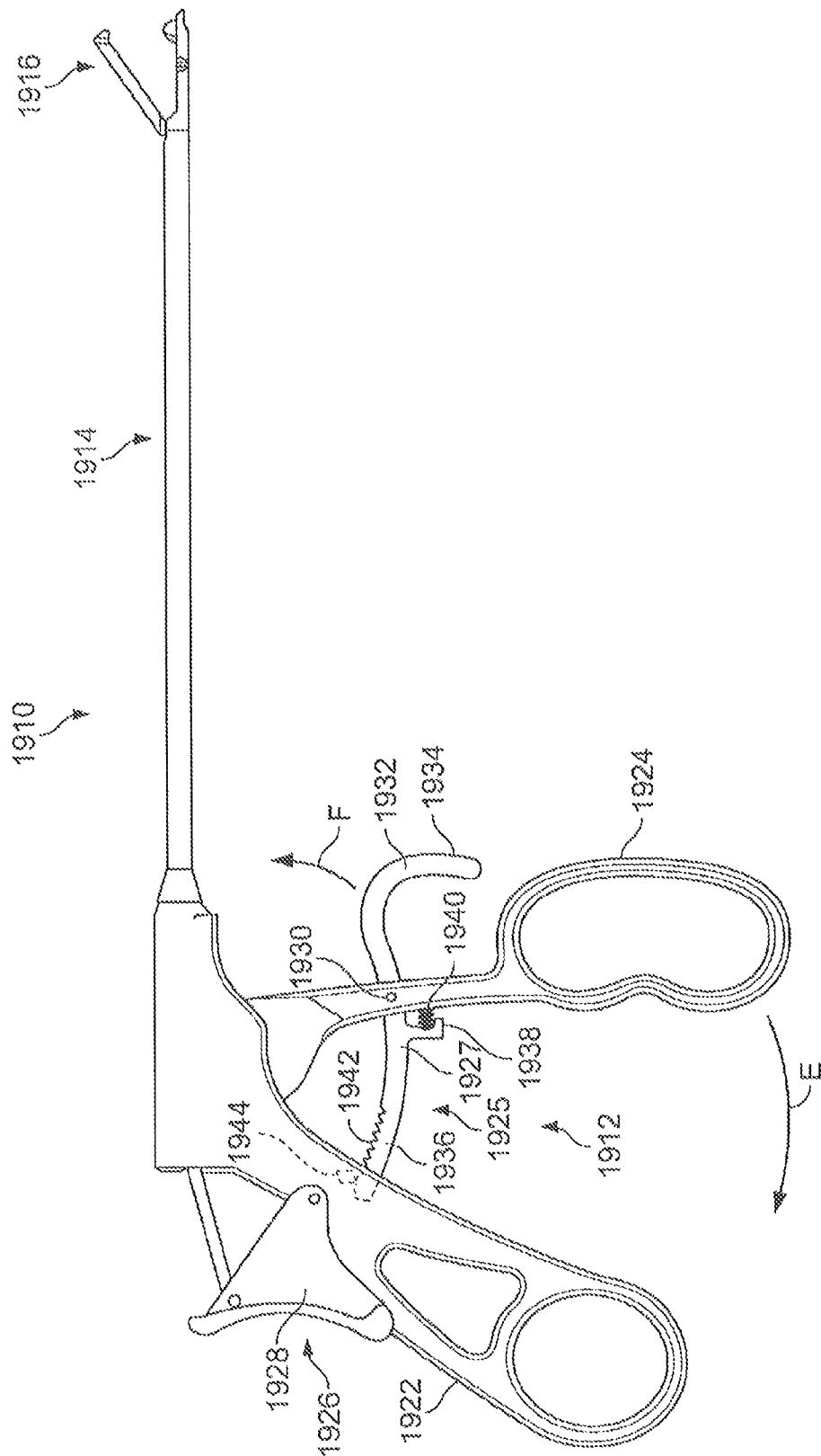
FIGS. 19 and 20 illustrate another implementation of a suture passing instrument.
Figure 20:
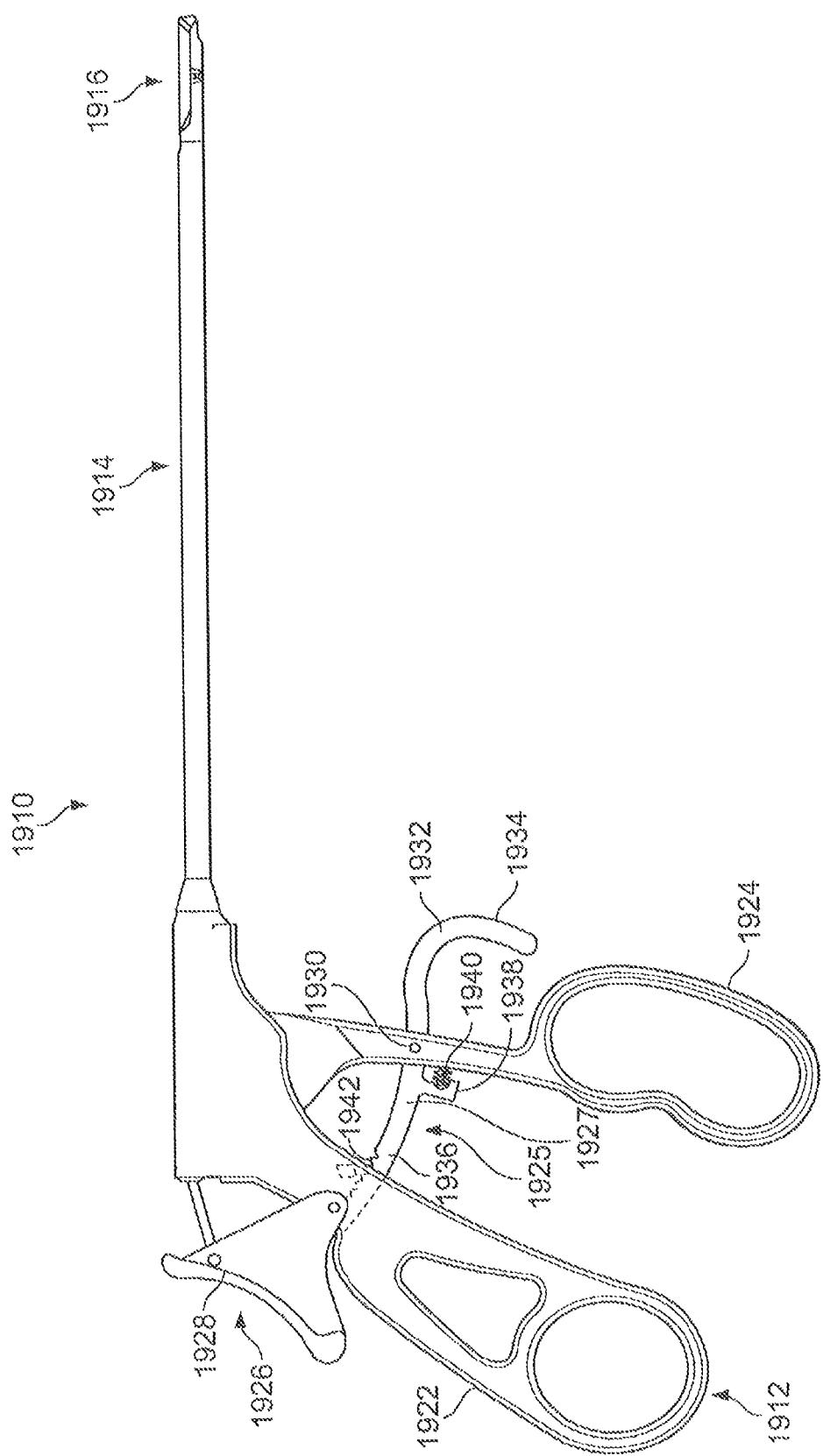

Referring to FIGS. 19 and 20, in an alternative embodiment, a suture passing instrument 1910 includes a handle 1912 having a moveable finger loop 1924 and a stationary thumb loop 1922, an elongated housing 1914, a distal jaw assembly 1916, and a needle actuating assembly 1926, and is analogous to previously described suture passing instrument 10 except for the following. First, unlike needle actuating assembly 26 that includes a needle driver 28 and a trigger 30 that can be actuated to move the needle 32, actuating assembly 1926 includes only a needle driver 1928 that is pivotally mounted to thumb loop 1922, but no trigger. Needle driver 1928 is analogous in operation to needle driver 28 of instrument 10.

Second, finger loop 1924 and thumb loop 1922 are joined by a locking mechanism 1925 so that the operator can lock the finger loop 1924 in a plurality of positions relative to thumb loop 1922. Locking mechanism 1925 includes a ratchet arm 1927 that is connected to finger loop 1924 by a pin 1930, which extends through bores in finger loop 1924 and ratchet arm 1927. Ratchet arm 1927 includes a distal portion 1932 that is curved to form a finger trigger 1934, a proximal portion 1936 with a plurality of teeth 1942 received within the slot formed in thumb loop 1922, and an extension 1938 that is connected to finger loop 1924 by a compression spring 1940. Teeth 1942 are engagable by a pawl 1944 disposed within slot 1941 in thumb loop 1922. In use, when the operator moves finger loop 1924 in a direction of arrow E to close the jaw assembly 1916, pawl 1944 engages teeth 1942 to prevent finger loop 1924 from moving in a direction opposite to arrow E. To release finger loop 1924, the operator moves trigger 1934 in the direction of arrow F, which disengages the teeth 1942 from the pawl 1944. To keep the teeth 1942 from inadvertently disengaging from pawl 1944, compression spring 1940 biases teeth 1942 against pawl 1944.

A number of implementations have been described. Nevertheless, it will be understood that various modifications may be made. For example, the pinless coupling of the upper and lower jaw can include projections on the lower jaw and corresponding openings in the upper jaw. The lower jaw or both jaws can be moveable. The actuator can be pinlessly coupled to a moveable lower jaw via a contoured groove on the lower jaw and a contoured distal portion of the actuator received in the contoured groove. The actuator can include a channel for receiving the stationary lower jaw shaft. The adaptor can include a different mechanical joint such as a linkage or a gear. In the handle, one or both of the thumb loop and the finger loop can be moveable to actuate the jaws. The moveable finger loop can be pinlessly coupled to the actuator by another mechanism such as a linkage or a gear. The needle actuator can include another mechanism for actuating the needle as a linkage or gear. The ratchet and the pawl can be located on opposite loops of the handle. Instead of a compression spring, the ratchet or the handle can include a portion, e.g., a leaf spring, that biases the ratchet. The needle can be flexible throughout its length or only at a distal portion received in the lower jaw. These and other implementations are within the scope of the following claims.

What is claimed is:

1. A surgical device comprising:
    a first member;
    a second member pivotably attached to the first member, the second member forming a distal end of a longitudinal shaft;
    a channel formed within the shaft extending from a proximal end of the shaft to an area proximal to the second member, the channel comprising a u-shaped lower surface extending between two walls of the shaft; and
    an actuator disposed within the channel of the shaft such that at least a portion of a body of the actuator extends into the channel and at least two extensions of the actuator extend outside of the channel;
    wherein the body of the actuator is spaced from the lower surface of the channel such that the body of the actuator and the lower surface of the channel define a longitudinally extending slot configured for receipt of a needle.

2. The device of claim 1, wherein the actuator is coupled to the first member such that axial movement of the actuator translates to pivotal movement of the first member relative to the second member.

3. The device of claim 1, wherein the at least two extensions are bendable from a first position, in which the at least two extensions are spaced from a top surface of the walls of the shaft, to a second position, in which the at least two extensions are in contact with the top surface of the walls of the shaft.

4. The device of claim 1, further comprising a needle disposed in the longitudinally extending slot.

5. The device of claim 4, wherein the needle is comprised of nitinol wire.

6. The device of claim 4, wherein the shaft is disposed within a cannulated outer cover.

* * * * *